US007371755B1

(12) United States Patent
Krippner et al.

(10) Patent No.: US 7,371,755 B1
(45) Date of Patent: May 13, 2008

(54) ANTIVIRAL AGENTS

(75) Inventors: Guy Krippner, Glen Waverley (AU); Phillip A. Reece, Balwyn (AU); Keith G. Watson, Surrey Hills (AU); Wen-Yang Wu, Mount Waverley (AU); Betty Jin, Mount Waverley (AU); Simon P. Tucker, Black Rock (AU)

(73) Assignee: Biota Scientific Management Pty Ltd., Notting Hill (AU)

( * ) Notice: Subject to any disclaimer, the term of this patent is extended or adjusted under 35 U.S.C. 154(b) by 77 days.

(21) Appl. No.: 10/088,282

(22) PCT Filed: Sep. 15, 2000

(86) PCT No.: PCT/AU00/01126

§ 371 (c)(1), (2), (4) Date: Jul. 22, 2002

(87) PCT Pub. No.: WO01/19822

PCT Pub. Date: Mar. 22, 2001

(30) Foreign Application Priority Data

Sep. 16, 1999 (AU) .................................... PQ2884

(51) Int. Cl.

| | |
|---|---|
| ***C07D 413/12*** | (2006.01) |
| ***C07D 413/14*** | (2006.01) |
| ***C07D 403/12*** | (2006.01) |
| ***C07D 409/12*** | (2006.01) |
| ***A61K 31/42*** | (2006.01) |
| ***A61K 31/496*** | (2006.01) |
| ***A61K 31/501*** | (2006.01) |
| ***A61K 31/787*** | (2006.01) |
| ***A61P 31/16*** | (2006.01) |

(52) U.S. Cl. ........................... 514/252.01; 514/252.12; 544/238; 544/359; 548/131; 548/240

(58) Field of Classification Search ................ 544/238, 544/359; 548/131, 240; 514/252.01, 252.12
See application file for complete search history.

(56) References Cited

U.S. PATENT DOCUMENTS

| | | | | |
|---|---|---|---|---|
| 4,818,761 | A * | 4/1989 | Sato et al. | 514/341 |
| 5,026,848 | A * | 6/1991 | Daneshtalab et al. | 544/137 |
| 5,637,708 | A * | 6/1997 | Hogle et al. | 546/140 |
| 6,355,807 | B1 * | 3/2002 | Tian et al. | 548/248 |
| 6,395,724 | B1 * | 5/2002 | Judice et al. | 514/183 |
| 6,420,354 | B1 * | 7/2002 | Marquess et al. | 514/183 |
| 6,420,560 | B1 * | 7/2002 | Numerof et al. | 544/362 |

FOREIGN PATENT DOCUMENTS

| | | | |
|---|---|---|---|
| WO | 9929280 | * | 6/1999 |
| WO | 9929908 | * | 6/1999 |
| WO | WO 99/29280 | | 6/1999 |
| WO | WO 99/29908 | | 6/1999 |
| WO | WO 99/64036 | | 12/1999 |
| WO | WO 00/55149 | | 9/2000 |

OTHER PUBLICATIONS

Hayden , F.G., Review in Medical Virology, 14, 17-31, 2004.*
Matrosovich, M.N., "Towards the Development of Antimicrobial Drugs Acting by Inhibition of Pathogen Attachment to Host Cells: A Need for Polyvalency," *Fed. of European Biochem. Soc.*, 252(1,2):1-4, 1989.
Spaltenstein, A. et al., "Polyacrylamides Bearing Pendant a-Sialoside Groups Strongly Inhibit a Agglutination of Erythrocytes by Influenza Virus," *J. Am. Chem. Soc.*, vol. 113, pp. 686-687, 1991.
Glick, G. et al., "Ligand Recognition by Influenza Virus. The Binding of Bivalent Sialosides," *J. of Bio. Chem.*, 266(35):23660-23669, Dec. 15, 1991.
Kramer, R. et al., "Spanning Binding Sites on Allosteric Proteins with Polymer-Linked Ligand Dimers," *Nature*, vol. 395, pp. 710-713, Oct. 15, 1998.
Mammen, M. et al., "Polyvalent Interactions in Biological Systems: Implications for Design and Use of Multivalent Ligands and Inhibitors," *Angew. Chem. Int'l Ed.*, vol. 37, pp. 2754-2794, 1998.

* cited by examiner

*Primary Examiner*—Venkataraman Balasubram
(74) *Attorney, Agent, or Firm*—Seed IP Law Group PLLC

(57) ABSTRACT

This invention relates to a compound capable of binding to a picornavirus capsid comprising two or more capsid binding moieties.

18 Claims, No Drawings

ANTIVIRAL AGENTS

This invention relates to antiviral agents, in particular to compounds useful in the treatment of infections caused by Picornaviridae, such as human rhinovirus (HRV). The invention also relates to the use of these compounds in the treatment of picornavirus infections and to intermediates useful in the preparation of those compounds. The invention is especially suitable for use in the treatment of HRV and accordingly it will be convenient to describe the invention in connection with these viruses. However it is to be understood that the invention is also applicable to other viruses of the Picornavirus family.

Human rhinovirus are a member of the genus *Rhinovirus* of the picornavirus family and are believed to be responsible for between 40 and 50% of common cold infections. Human rhinoviruses comprise a group of over 100 serotypically distinct viruses and accordingly antiviral activity for multiple serotypes and potency are considered to be equally important factors in drug design.

Two cellular receptors have been identified to which almost all typed HRVs bind. The major group, which comprises 91 of the more than 100 typed serotypes, binds to the intracellular adhesion molecule-1 (ICAM-1) while the minor group, which comprises the rest of typed serotypes with the exception of HRV87, binds to the low density lipoprotein receptor family of proteins.

The HRVs can also be divided into two groups, A and B, based on their sensitivity to 15 different capsid-binding antiviral compounds. Group A serotypes, such as HRV3 and HRV14, are more sensitive to long capsid binding compounds, while group B serotypes, such as HRV1A and HRV16, are more sensitive to short capsid binding compounds.

HRVs possess a single stranded (+) RNA genome which is about 7.2 kb in length. It is encapsidated by a protein shell (or capsid) having pseudo icosahedral symmetry and which is composed of sixty copies of each of four different viral proteins, VP1-VP4. Proteins VP1, VP2 and VP3 each have a molecular weight of about 30 kDa and are folded into an eight stranded antiparallel beta-barrel motif, while VP4, which lines the internal surface of the capsid, has a molecular weight of 7 KDa. These eight strands form two opposing sheets, referred to as "BIDG" and "CHEF". The BIDG sheet faces predominantly towards the interior while the CHEF sheet is more exposed on the exterior.

The surface of the capsid contains "canyons" have a depth of approximately 15 Å which surround each of the icosahedral fivefold axes. Residues lining the canyon floor are more conserved than other surface residues and accordingly it is proposed that the cellular receptor binds to residues on the canyon floor. Since these residues are inaccessible to antibodies due to steric hindrance they would allow the virus to escape host immune surveillance.

A hydrophobic pocket lies underneath the canyon between the BIDG and CHEF sheets of VP1. There are a number of antiviral compounds which are capable of binding within this pocket and may cause conformational changes. Some of these compounds have been shown to inhibit the uncoating of HRVs and, for some of the major receptor group viruses, inhibition of cell receptor binding has also been demonstrated. It has also been shown that when a compound is bound within the hydrophobic capsid pocket, HRVs are more stable to denaturation by heat or acids.

The hydrophobic pocket can be divided into two regions, the pore and the hydrophobic region. Both the pore and the hydrophobic region can accommodate a wide range of structures, as evidenced by the diverse range of compounds which are known to bind in the pockets. It has even been found that molecules of a similar structural class can bind in different orientations.

In some HRVs, such as naturally occurring HRV1A and HRV16, the hydrophobic pocket is filled with an elongated hydrophobic molecule, postulated to be a fatty acid. These molecules are referred to as "pocket factors", and their presence is believed to stabilize the capsid protein and provide for better transmission from one host to another. While pocket factors are not found in purified HRV3 or HRV14, this may be due to the purification process, and poorer hydrophobic interactions.

When HRVs bind to cells they are first converted to "A" (altered) particles which lack VP4. These A particles subsequently lose RNA and form empty particles.

Another factor which is believed to stabilize the capsid is the presence of amphipathic helices in the N-terminus of VP1, which occurs in HRV16, compared to the disordered N-terminus of VP1 in HRV3 and HRV14. Interaction between the amphipathic helices of VP1 and the VP4 may stabilize the capsid and hinder the ejection of VP4 on binding to cells or soluble ICAM-1. This is consistent with the greater stability of HRV16 compared to HRV3 and HRV14.

Various studies have been undertaken to determine the conformation of different capsid binding compounds within the hydrophobic pocket, and the conformational changes in the capsid proteins caused by the presence of capsid binding compounds within the hydrophobic pockets.

In general the binding of a compound within the hydrophobic pocket causes enlargement of the pocket and reduction of the pore. The orientations of various capsid binders bound in the hydrophobic pocket of several of the picornavirus family have been determined through crystallographic studies and are detailed in Table 1. Antiviral drugs made by Sterling-Winthrop Pharmaceuticals are designated by "WIN" numbers (based on oxazolinyl isoxazoles), those from Janssen Research Foundation are designated by "R" numbers (based on pyridazinamines), those from Sandoz Forschungsinstitut are designated by "SDZ" numbers, those from Schering-Plough are designated by "SCH" numbers.

TABLE 1

| Compound name | Structure: Heel … Toe | Picornavirus | Ref. |
| --- | --- | --- | --- |
| SCH 38057 | 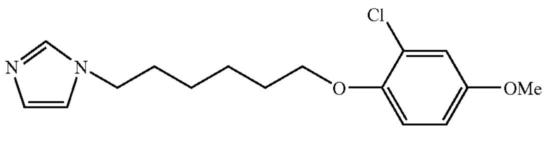 | HRV 14 | 1 |

TABLE 1-continued
| Compound | Structure | | | |
|---|---|---|---|---|
| name | Heel Toe | | Picornavirus | Ref. |
| SCH 48973 | 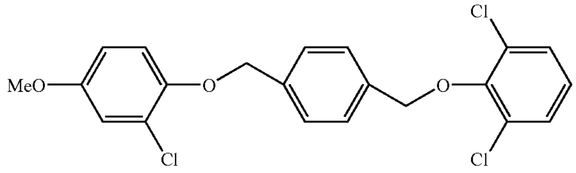 | | Polio 2 | 2 |
| R 61837 | 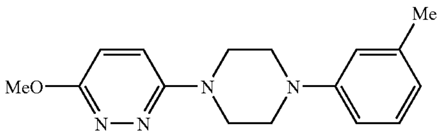 | | HRV 14 | 3,4 |
| R 77975 | 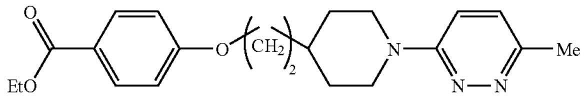 | | Polio 3 | 5 |
| R 76206 | 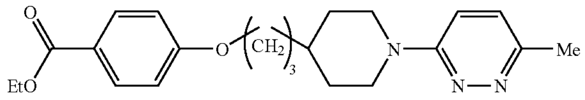 | | Polio 1,3 | 5 |
| R 80633 | 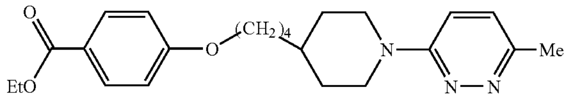 | | Polio 3 | 5 |
| SDZ 880 061 | 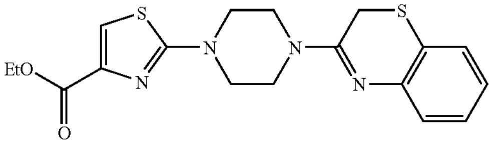 | | HRV 14 | 6 |
| SDZ 35682 | 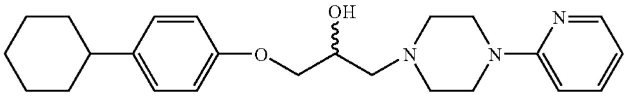 | | HRV 14 | 7 |
| WIN 52084-S | 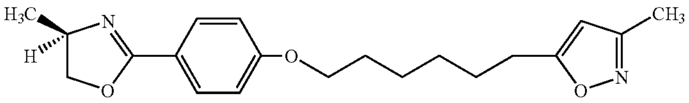 | | HRV 14 | 8 |
| WIN 51711 | 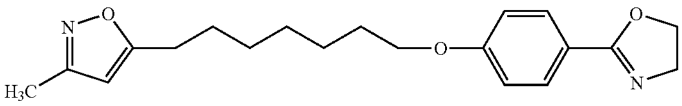 | | HRV 14 | 8 |
| WIN 54594 | 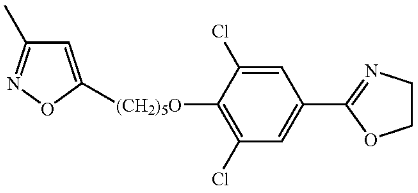 | | HRV 1A, 14 | 3 |

TABLE 1-continued

| Compound name | Structure Heel | Toe | Picornavirus | Ref. |
|---|---|---|---|---|
| WIN 56291 | 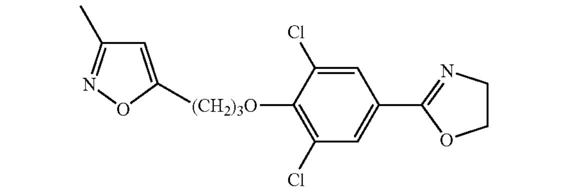 | | HRV 1A, 3, 14 | 3 |
| WIN 52452 | 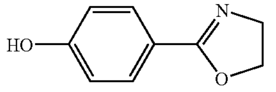 | | HRV 14 | 9 |
| WIN 61605 | 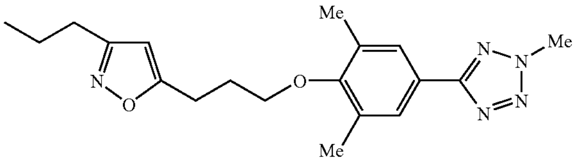 | | HRV 14 | 10 |

1. Zhang, A. et al. J. Mol. Biol. 230 (1993) 857-867
2. Lentz. Structure J. Mol. Biol. 5 (1997) 961
3. Kim, K. H. et al. J. Mol. Biol. 230 (1993) 206-227
4. Chapman, M. S. et al. J. Mol. Biol. 217 (1991) 455-463
5. Grant, R. A. et al. Current Biology 4 (1994) 784-797
6. Oren, D. A. et al. J. Mol. Biol. 259 (1996) 120-134
7. Rosenwirth, B. et al. Antiviral Res. 26 (1995) 55-64
8. Badger, J. et al. Proc. Natl. Acad. Sci. 85 (1988) 3304-3308
9. Bibler-Muckelbauer, J. K. et al. Virology 202 (1994) 360-369
10. Giranda et al. Acta Cryst. D51 (1995) 496

The interactions between capsid binding drugs and virus are predominantly hydrophobic in nature. In serotype 14, the most active antiviral agents of the WIN series have 7-carbon long aliphatic chains. In contrast, the best antivirals for serotypes 1A and 16 have aliphatic chains less than or equal to 5 carbons long between the aromatic rings. The particular orientation of each drug in the pocket is not predictable. In contrast to the WIN and R compounds which occupy space nearest the pocket entrance, the SCH drug leaves a large open space near the entrance.

While binding and viral inhibition appears promising from in vitro testing, and some have been nominated for clinical trials and challenge studies, the capsid binding compounds have not proved useful in animal models or human trials (see for example R. B. Turner et al., Antimicrobial Agents and Chemotherapy, 1993, 37, 297-300). Some trials have shown a reduction in viral shedding, but the symptoms have still remained (E. Arruda et al., The Journal of Infectious Diseases, 1995, 171, 1329-1333).

In addition to showing good potency through binding and inhibition, any candidate drug must also be non-toxic, have favourable pharmacokinetic properties and should preferably have a broad spectrum of antirhinoviral activity.

It is an object of the present invention to overcome or at least alleviate one or more of the problems with the prior art capsid binding compounds, or to provide the public with a useful choice.

According to the present invention there is provided a compound capable of binding to a picornavirus capsid comprising two or more capsid binding moieties. Preferably the capsid is a HRV capsid.

As used herein the term “capsid binding moiety” refers to a portion or substituent of said compound which is capable of binding within the hydrophobic pocket of the VP1 protein of a picornavirus capsid.

The capsid binding moiety may be a functional binding residue of a HRV capsid binding compound.

As used herein the terms “picornavirus capsid binding compound” and “HRV capsid binding compound” refer to a compound capable of binding inside the hydrophobic capsid pocket within the VP1 protein of the picornavirus or HRV capsid.

As used herein the term “functional binding residue of a picornavirus capsid binding compound” refers to a residue of a picornavirus capsid binding compound which is capable of binding inside the hydrophobic capsid pocket despite being attached to another chemical entity. It is to be understood that attachment to another chemical entity may result in a reduction of binding strength in the pocket relative to the capsid binding compound from which the residue is derived.

The capsid binding moieties are preferably covalently attached to a non-polymeric backbone or core, such that two or more of the capsid binding moieties are able to bind within separate hydrophobic pockets on the same or different HRV capsids simultaneously.

As used herein the term “non polymeric backbone or core” refers to a chemical moiety of defined structure capable of supporting two or more capsid binding moieties in defined positions. The non-polymeric backbone or core will generally have a molecular weight of less than 10,000, and preferably has an axis or centre of symmetry.

Examples of suitable non-polymeric backbones and cores include those derived from straight chain, branched or cyclic $C_1$-$C_{70}$ alkyl (optionally including one or more double or triple bonds or aryl groups) which may include one or more heteroatoms selected from oxygen, sulphur and nitrogen; oligomers of amino acids such as glycine, alanine, lysine, glutamic acid and aspartic acid, acrylamide and N-substituted acrylamides, acrylic acid, alkyleneoxy units such as ethylene glycol, aminoalkanoic acids such as 6-aminocaproic acid, N,N'-dialkylureas, carbohydrates such as glucose, and other oligopeptides and oligosaccharides; small to medium sized dendritic cores; and cyclodextrins. The backbone or core preferably includes two or more linker groups to which the capsid binding moieties are attached. The linker groups should be of sufficient length to allow the capsid binding moiety to reach inside one of the hydrophobic pockets of the capsid. The linker group should be capable of passing through the pore without preventing binding of the moiety within the pockets. As mentioned above, in the case of residues of capsid binding compounds, some reduction of binding strength in the pocket may occur relative to the capsid binding compound itself. Suitable linker groups include, but are not limited to alkyl, aryl, alkenyl, alkynyl, alkyleneoxy, amino acids, alkylamino, alkylcarbonyl, alkylcarboxy, alkoxy, alkylurea, alkylhydrazide (and combinations of any of these). In a preferred embodiment the backbone, linker or both contains functional groups or moieties that impose some restrictions on available degrees of freedom. Examples of such groups or moieties include alkenyl, aryl and amido groups.

According to another aspect of the present invention there is provided a compound capable of binding to a picornavirus capsid comprising a non polymeric backbone or core to which two or more capsid binding moieties are covalently attached. In view of the non-polymeric nature of the backbone or core the compounds according to the invention will generally have a discrete molecular structure, producing a discrete molecular ion when analysed by a mass spectrometer.

The compounds according to the invention will generally have between two and ten, more preferably between two and five, capsid binding moieties. In a particularly preferred embodiment the compound includes five capsid binding moieties located on the backbone or core in such a manner that they bind within the five hydrophobic pockets located about one of the fivefold icosahedral axes of the capsid.

In another preferred embodiment the compound according to the invention is in the form of a "dimer", having an even number of capsid binding moieties, preferably two or four and most preferably two. These symmetrical dimeric compounds may be prepared by dimerizing a compound having one or more capsid binding moieties using techniques which would be apparent to those skilled in the art.

The capsid binding moieties may be derived from any of the known picornavirus capsid binding compounds, or from any compound capable of binding within the hydrophobic capsid pocket of one or more of the serotypes of HRV.

The capsid binding moieties may be derived from any of the WIN, Janssen R, SDZ or SCH compounds referred to above or any functional derivatives thereof. Other suitable capsid binding compounds include chalcone amides, flavones, flavans, chalcone compounds as described in Burgers Medicinal Chemistry, vol. 5, Chapter 4, pages 595-601, and the compounds described in K. Andries et al., *Antiviral Research,* 16, 213 (1991) and G. D. Diana et al., *Antiviral Chemistry & Chemotherapy,* 8, 401 (1997). Specific examples of capsid binding moieties include Pirodavir, Pleconaril, Win 54954, Win 61605 and its biphenyl analogue, and R61837.

In a preferred embodiment the picornavirus capsid binding compounds from which the capsid binding moieties may be derived are of the formula (I)

$$Ar^1(X)_mW(Y)_nAr^2 \qquad (1)$$

where $Ar^1$ and $Ar^2$ are optionally substituted aryl groups, which may be the same or different;

X and Y are independently selected from O, S, CO, C(O)O, CONR or NR, where R is hydrogen or $C_{1-6}$ alkyl; and W is a divalent spacer group; and m and n are independently 0 or 1.

As used herein the term "aryl groups" refers to aromatic rings or ring systems. The aromatic rings may be carbocyclic, heterocyclic or pseudo aromatic, and may be mono-, bi- or tri-cyclic ring systems. The aromatic rings or ring systems are generally composed of 3 to 15 carbon atoms and, in the case of hetero aromatic rings, may contain one or more heteroatoms selected from N, S and O. Examples of suitable rings include but are not limited to benzene, biphenyl, naphthalene, tetrahydronaphthalene, anthracene, dihydroanthracene, pyridine, thiophene, benzothiophene, furan, isobenzofuran, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, oxazole, oxadiazole, tetrazole, thiazole, isothiazole, isooxazole, phenoxazine and the like, each of which may be optionally substituted. The term "pseudoaromatic" refers to a ring system which is not strictly aromatic, but which is stablized by means of delocalization of electrons and behaves in a similar manner to aromatic rings. Examples of pseudoaromatic rings include but are not limited to furan, thiophene, pyrrole and the like.

Preferred aryl groups include benzene, pyridine, pyridazine, pyrazine, pyrimidine, 1,2,4-triazine, furan, thiophene thiazole, isothiazole, isoxazole, 1,2,4-triazole, oxazole, imidazole, pyrazole, 1,4-benzothiazine, indole and benzofuran.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkoxyamino, alkenyloxy, aryloxy, benzyloxy, haloalkoxy, haloalkenyloxy, haloaryloxy, cyano, carboxyl, nitro, amino, alkylamino, dialkylamino, alkenylamino, alkynylamino, arylamino, diarylamino, benzylamino, acyl, alkenylacyl, alkynylacyl, arylacyl, acylamino, heterocyclyl, heterocycloxy, heterocyclamino, haloheterocyclyl, carboalkoxy, carboaryloxy, alkylthio, alkylsulfonyl, alkylsulfinyl, benzylthio and sulphonamido. Where the substituent includes an aromatic or heterocyclic aromatic ring, that ring may be substituted with one or more groups selected from alkyl, alkenyl, alkynyl, halo, haloalkyl haloalkenyl, haloalkynyl, hydroxy, alkoxy and alkenyloxy. Preferred heterocyclyl substituents include oxazole, dihydrooxazolyl, thiazolyl, 1,2,4-oxadiazolyl, 1,2,4-thiadiazolyl, 1,2,4-triazolyl and tetrazolyl.

In the above definitions, the term "alkyl", used either alone or in compound words such as "alkenyloxyalkyl", "alkylthio", "alkylamino" and "dialkylamino" denotes straight chain, branched or cyclic alkyl, preferably $C_{1-6}$ alkyl or cycloalkyl. Examples of straight chain and branched alkyl include methyl, ethyl, propyl, isopropyl, butyl, isobutyl, sec-butyl, t-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl and 1,1,2-trimethylpropyl. Examples of cyclic alkyl include groups such as cyclopropyl, cyclobutyl, cyclopentyl, cyclohexyl, cycloheptyl, cyclooctyl, cyclononyl, cyclodecyl and the like.

The term "alkoxy" denotes straight chain or branched alkoxy, preferably $C_{1-4}$ alkoxy. Examples of alkoxy include methoxy, ethoxy, n-propoxy, isopropoxy and the different butoxy isomers.

The term "alkenyl" denotes groups formed from $C_{2-6}$ straight chain, branched or cyclic alkenes. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1,3-butadienyl, 1-4,pentadienyl, 1,3-cyclopentadienyl, 1,3-hexadienyl, 1,4-hexadienyl, 1,3-cyclohexadienyl and 1,4-cyclohexadienyl.

The term "alkynyl" denotes groups formed from straight chain or branched groups as previously defined which contain a triple bond, preferably $C_{2-6}$ alkynyl. Examples of alkynyl include ethynyl, 2,3-propynyl and 2,3- or 3,4-butynyl.

The term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-8}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl and octanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl and toluoyl; aralkanoyl such as phenylalkanoyl (e.g. phenylacetyl), aryloxyalkanoyl (such as phenoxyacetyl); arylsulfonyl such as phenylsulfonyl; heterocycliccarbonyl; heterocyclicalkanoyl such as thienylacetyl, thienylpropanoyl and thienylbutanoyl and heterocyclicalkenoyl such as heterocyclicpropenoyl and heterocyclicbutenoyl.

The term "divalent spacer group" as used herein refers to a divalent group interposed between the two aryl groups. The spacer group should be of a size which allows the compound to bind within the capsid pocket. Examples of suitable divalent spacer groups include optionally substituted straight chain or branched alkylene groups of from 1 to 10 carbon atoms which may have one or more double or triple bonds; optionally substituted alkyleneoxy groups; optionally substituted aryl groups; and optionally substituted aliphatic rings which may be saturated or unsaturated and which may include one or more heteroatoms selected from O, S and N.

Preferably the spacer is selected from $-(CH_2)_m-$ where m is 1 to 9; $-(CH_2)_p-Z-(CH_2)_q-$, where Z is an optionally substituted $C_2$-$C_6$ alkylene group containing one or more double or triple bonds; or a 5 or 6-membered aromatic or aliphatic ring which may contain one to four heteroatoms selected from O, S and N, and p and q are independently 0 to 4.

Preferably the spacer is selected from $-(CH_2)_m-$ where m is 2 to 7; a group of the formula $-(CH_2)_p-Z-(CH_2)_q-$ where p and q are independently 0 to 3 and Z is a five or six membered aromatic or aliphatic ring containing from 1 to 2 N atoms, or a group of the formula $-(CH{=}CH)_r-$ where n is 1 to 3.

Other capsid binding compounds which do not fall within the scope of formula (I) may also be used to provide the capsid binding moieties of the present invention. Examples of other such capsid binding compounds include long chain fatty acids and esters, flavanone and flavan derivatives.

The overall size of the capsid binding moiety will need to be such that it is capable of binding substantially within the hydrophobic pocket.

The compounds of the invention may also be used in diagnostic methods, in particular methods for the detection of picornavirus. For use in such methods it may be advantageous to link a compound of the invention to a detectable label such as a gold, biotin, radioactive, fluorescent, or chemiluminescent label. The person skilled in the art will be aware of the wide variety of suitable labels. The label may be attached to the non-polymeric backbone or core of the compound such that the label is exposed when the compound binds to a picornavirus capsid. The label is preferable a biochemically active label such as Biotin, a radioactive or fluorescent label or a functional group which would allow direct conjugation to an enzyme or antibody. For examples, see Bioconjugate Techniques by G. T. Hermanson (1996).

Picornavirus may be detected using compounds of the invention as follows. Compounds (such as compound 60) are incubated with a mixture containing picornavirus under suitable conditions to permit the binding of the compounds to the picornavirus capsid. The virus-compound complex is localised via non-specific (eg. nitrocellulose), or specific interactions (eg. antibody-biotin or streptavidin-biotin) onto a solid surface and the complex detected via the label attached to the compound. The person skilled in the art will be aware of the many variations of this method that are possible and, through existing knowledge or experimentation, arrive at the most suitable for the desired diagnositic device (eg. ELISA, flow through chromatographic strip, etc.).

The compounds according to the invention may be prepared in a number of different ways depending on the nature of the backbone or core, and the nature of the capsid binding moieties. The capsid binding moieties may be obtained through commercial sources or may be prepared in accordance with methods described in the literature, for example in J. Medicinal Chemistry, 38, pages 1355-71 and 2780-83 (1995); Antiviral Chemistry & Chemotherapy, 6, 245-254 (1995); J. Molecular Biology, 259, 120-134 (1996); and U.S. Pat. Nos. 5,001,125 and 4,992,433.

The capsid binding moieties are preferably covalently attached to the rest of the compound (i.e. the backbone or core) at a position on the capsid binding moiety located in the region of the "heel" of the capsid binding compound from which the moiety is derived. As used herein the term "heel" refers to the end of a capsid binding compound which lies near the pore of the hydrophobic pocket (i.e. near the pocket entrance) while the term "toe" refers to the end which extends into the inner region of the hydrophobic pocket. The orientation of the capsid binding compounds within the hydrophobic pocket of a picornavirus capsid can be determined by X-ray crystallography using standard techniques. The orientation of many capsid binding compounds has already been determined as indicated in Table 1 above.

To facilitate attachment of the capsid binding compound to the backbone or core it is preferred that the capsid binding compound contains a functional group at the heel region capable of forming a bond with another chemical entity, which may be all or part of the backbone or core. If the capsid binding compound does not include such a functional group, then one may be introduced using standard techniques. Such a functionalised derivative of a capsid binding compound is to be understood to be encompassed by the term "capsid binding compound". It is also possible to convert substituents present on the capsid binding moiety to functional groups capable of forming a bond with the backbone or core. Examples of suitable functional groups include, but are not limited to hydroxy, amine, azide, aldehyde, carboxylic acid and derivatives thereof, such as amides and esters, hydrazide, oxime ethers, imidazolide, hydroxamate, thioester, and acid chloride; mercapto, halide, ketone, hydrazine, isocyanate and isothiocyanate.

A linker group may be attached to the capsid binding compound by reaction with the functional group. This may proceed in stages (by chain extension processes) or the core or backbone may be attached as a complete unit. The intermediate capsid binding moiety with core/backbone attached may then be reacted with one or more further functionalised capsid binding moieties, or may be dimerized. These intermediates are novel and represent a further aspect of the present invention. The intermediates may be attached to a detachable label to provide a diagnostic as described above.

Some examples of such novel intermediates are shown below in Table 2.

TABLE 2

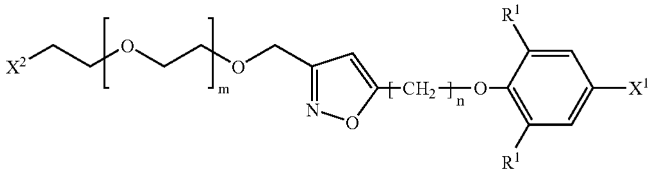

| Compound number | R1, R2 | m | n | $X^1$ | $X^2$ |
|---|---|---|---|---|---|
| 1 | Cl | 3 | 5 | 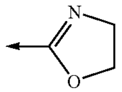 4,5-dihydrooxazoline-2- | $N_3$ |
| 2 | Cl | 3 | 5 | 4,5-dihydrooxazoline-2- | $NH_2$ |
| 3 | Cl | 3 | 5 | 4,5-dihydrooxazoline-2- | FmocNH |
| 4 | Cl | 3 | 5 | 4,5-dihydrooxazoline-2- | Fmoc-(Glycine)$_3$NH |
| 5 | Cl | 3 | 5 | 4,5-dihydrooxazoline-2- | Fmoc-(6-amino-caproamido)$_2$NH |
| 6 | | | | 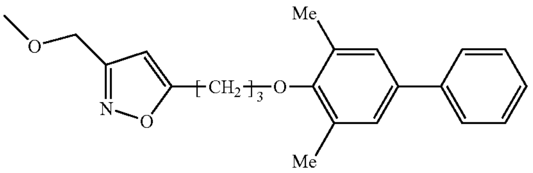 | |
| 7 | Me | 1 | 3 | Phenyl | OH |
| 8 | Me | 2 | 3 | Phenyl | OH |
| 9 | Me | 3 | 3 | Phenyl | OH |
| 10 | Me | 5 | 3 | Phenyl | OH |
| 11 | Me | $7^1$ | 3 | Phenyl | OH |
| 12 | Me | $10^1$ | 3 | Phenyl | OH |
| 13 | Me | $19^1$ | 3 | Phenyl | OH |
| 14 | Me | 1 | 3 | Phenyl | $NH_2$ |
| 15 | Me | 2 | 3 | Phenyl | $NH_2$ |
| 16 | Me | 3 | 3 | Phenyl | $NH_2$ |
| 17 | Me | 5 | 3 | Phenyl | $NH_2$ |
| 18 | Me | 5 | 3 | Phenyl | $H_2N—(CH_2CH_2O)_6$-1,4-$CH_2C_6H_4CH_2O—$ |
| 19 | Me | 1 | 3 | Phenyl | AcNH |
| 20 | Me | 2 | 3 | Phenyl | AcNH |

TABLE 2-continued

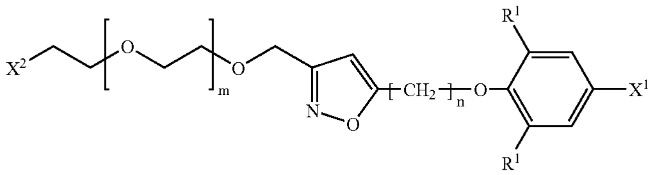

| Compound number | R1, R2 | m | n | $X^1$ | $X^2$ |
|---|---|---|---|---|---|
| 21 | Me | 3 | 3 | Phenyl | AcNH |
| 22 | Me | 5 | 3 | Phenyl | AcNH |
| 23 | Me | 1 | 3 | 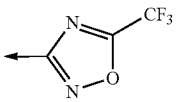 5-trifluoromethyl-1,2,4-oxadiazoline-3- | OH |
| 24 | Me | 2 | 3 | 5-trifluoromethyl-1,2,4-oxadiazoline-3- | OH |
| 25 | Me | 3 | 3 | 5-trifluoromethyl-1,2,4-oxadiazoline-3- | OH |
| 26 | Me | 5 | 3 | 5-trifluoromethyl-1,2,4-oxadiazoline-3- | OH |
| 27 | 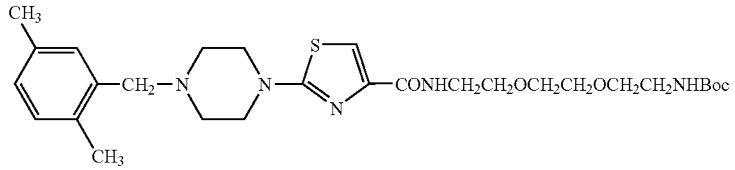 | | | | |
| 28 | 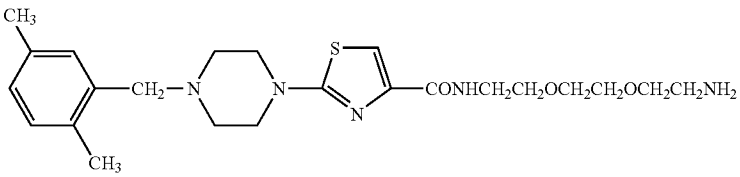 | | | | |
| 29 | 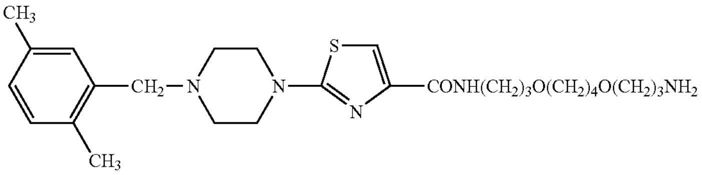 | | | | |
| 30 | 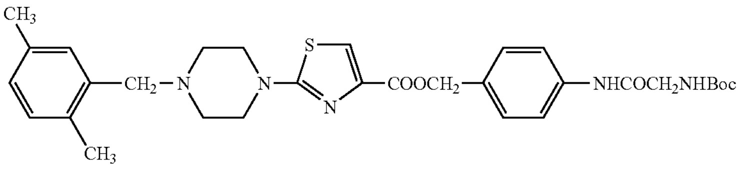 | | | | |

[1]Prepared from PEG mixtures of narrow distribution. For convenience m represents the mean number of glycol units.

In another method the functional group on the capsid binding compound may be extended as described above, and may then be reacted with a core or backbone containing functional groups capable of forming a bond with the extended group attached to the capsid binding moiety.

In a further method the functionalised capsid binding moieties may be reacted directly with a core or backbone containing functional groups capable of forming a bond with the functional groups on the capsid binding compounds.

Other methods of preparing the compounds according to the present invention would be evident to a person skilled in the art.

Some examples of compounds according to the invention are shown below in Table 3.

TABLE 3
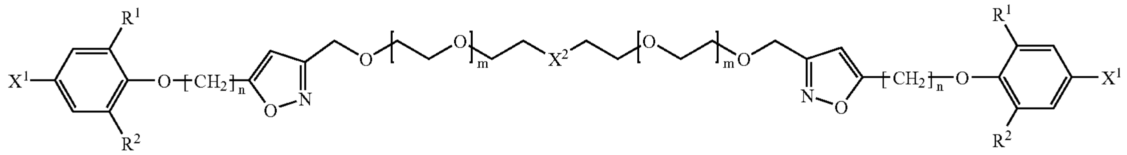
| Compound number | Substituent R1, R2 | m | n | $X^1$ | $X^2$ |
|---|---|---|---|---|---|
| 31 | Cl | 3 | 5 | 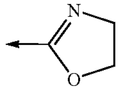 4,5-dihydrooxazoline-2- | $NHCOCH_2O—(CH_2CH_2O)_9CH_2CONH—$[1] |
| 32 | 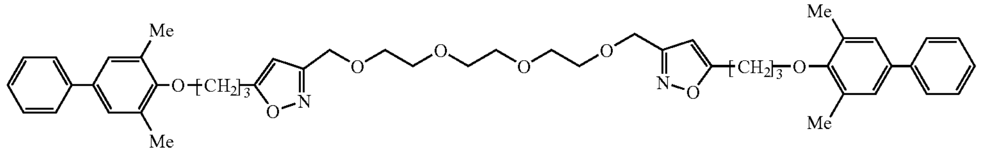 | | | | |
| 33 | Me | 1 | 3 | Phenyl | O |
| 34 | Me | 2 | 3 | Phenyl | O |
| 35 | Me | 3[1] | 3 | Phenyl | O |
| 36 | Me | 5[1] | 3 | Phenyl | O |
| 37 | Me | 9[1] | 3 | Phenyl | O |
| 38 | Me | 1 | 3 | Phenyl | 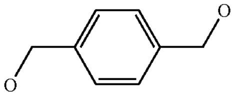 |
| 39 | Me | 2 | 3 | Phenyl | " |
| 40 | Me | 3 | 3 | Phenyl | " |
| 41 | Me | 5 | 3 | Phenyl | " |
| 42 | Me | 1 | 3 | Phenyl | 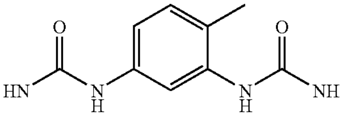 |
| 43 | Me | 2 | 3 | Phenyl | " |
| 44 | Me | 3 | 3 | Phenyl | " |
| 45 | Me | 5 | 3 | Phenyl | " |
| 46 | Me | 1 | 3 | Phenyl | 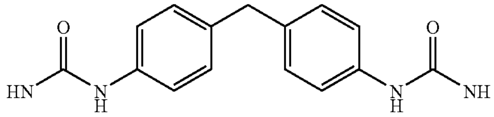 |
| 47 | Me | 2 | 3 | Phenyl | " |
| 48 | Me | 3 | 3 | Phenyl | " |
| 49 | Me | 5 | 3 | Phenyl | " |
| 50 | Me | 0 | 3 | 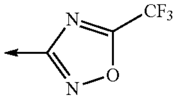 5-trifluoromethyl-1,2,4-oxadiazoline-3- | O |
| 51 | 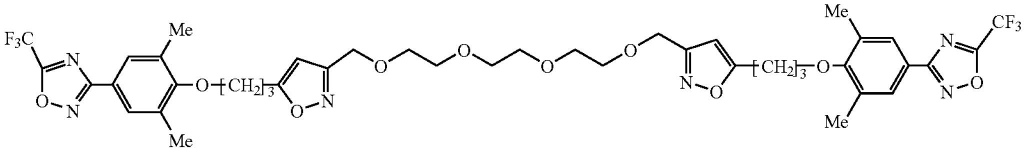 | | | | |

TABLE 3-continued
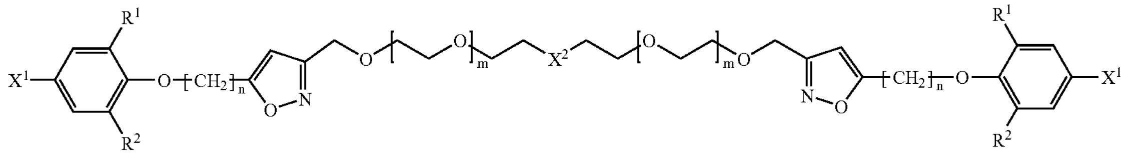
| Compound number | Substituent R1, R2 | m | n | $X^1$ | $X^2$ |
|---|---|---|---|---|---|
| 52 | Me | 1 | 3 | 5-trifluoromethyl-1,2,4-oxadiazoline-3- | O |
| 53 | Me | 2 | 3 | 5-trifluoromethyl-1,2,4-oxadiazoline-3- | O |
| 54 | Me | 1 | 3 | 5-trifluoromethyl-1,2,4-oxadiazoline-3- | 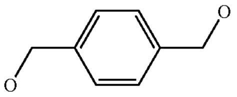 |
| 55 | Me | 2 | 3 | 5-trifluoromethyl-1,2,4-oxadiazoline-3- | " |
| 56 | Me | 3 | 3 | 5-trifluoromethyl-1,2,4-oxadiazoline-3- | " |
| 57 | Me | 5 | 3 | 5-trifluoromethyl-1,2,4-oxadiazoline-3- | " |
| 58 | 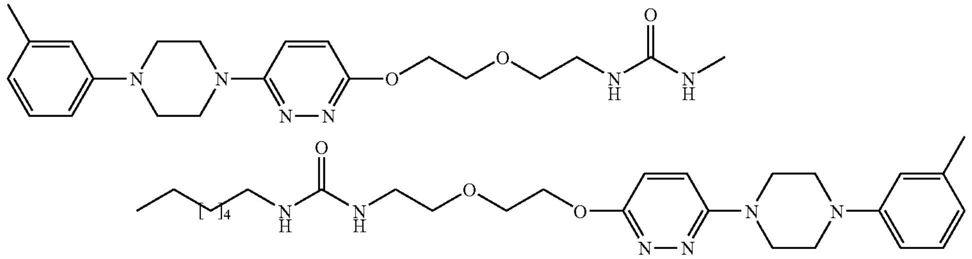 | | | | |
| 59 | 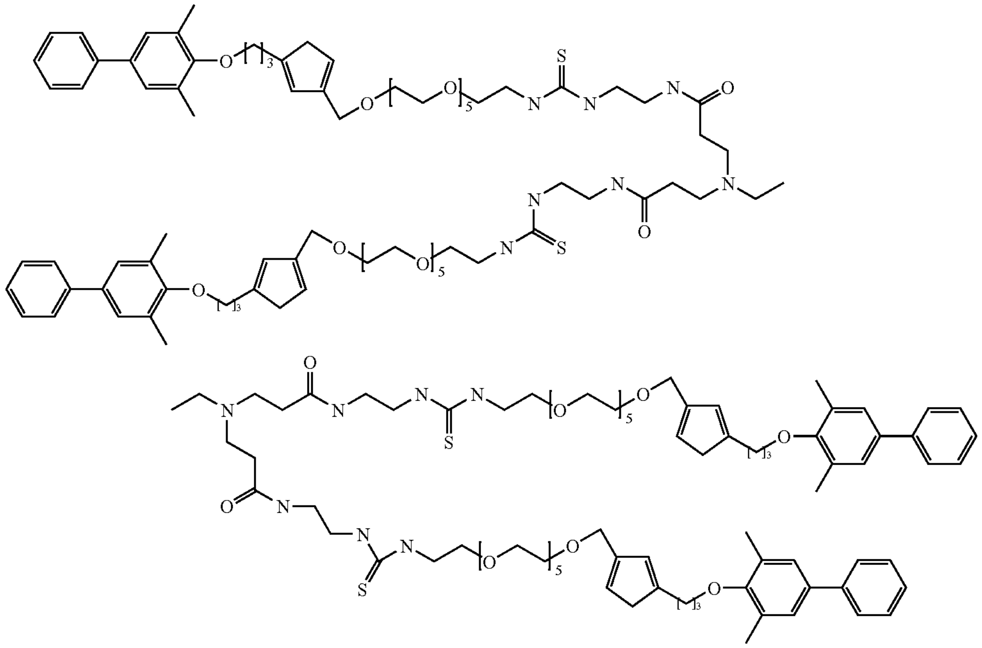 | | | | |

TABLE 3-continued

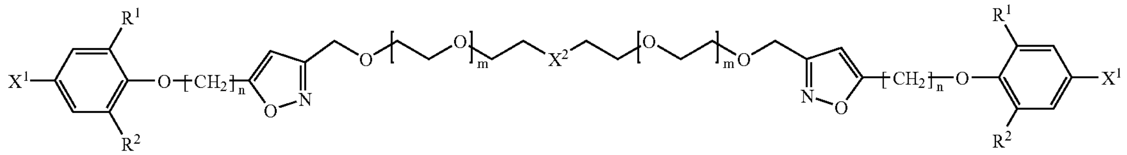

| Compound number | Substituent R1, R2 | m | n | $X^1$ | $X^2$ |
| --- | --- | --- | --- | --- | --- |
| 60 | 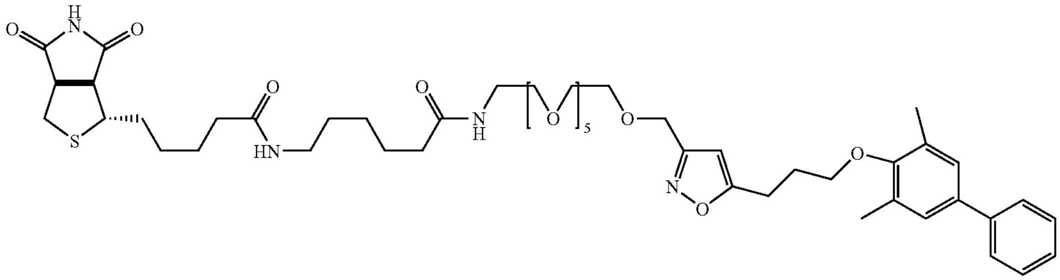 | | | | |
| 61 | 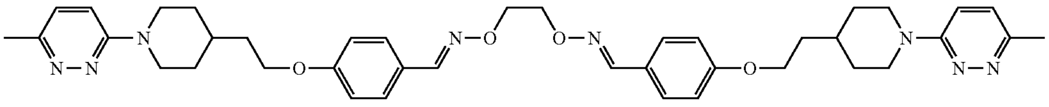 | | | | |

[1]Prepared from PEG mixtures of narrow distribution. For convenience m represents the mean number of glycol units.

As mentioned above, rhinoviruses can be divided into two categories (designated A and B) based on their susceptibility to various classes of capsid binder. Accordingly flavans and the Janssen pyridazines are active almost exclusively against rhinovirus serotypes from category B whereas the WIN family of compounds is generally more active against the category A rhinoviruses (see Antiviral Res. 16 (1991) 213-225.)

The present invention also allows for the presence of different capsid binding compounds on the one backbone or core which provides for a greater antiviral spectrum of activity.

It is also possible to introduce other groups, such as hydrophilic sugars or charged groups, into the compounds to alter their solubility characteristics.

The compounds according to the present invention are useful in the treatment of picornaviral infections in mammals, preferably humans.

The picornavirus infection may be caused by any virus of the family Picornaviridae. Representative family members include human rhinoviruses, polioviruses, enteroviruses including coxsackieviruses and echoviruses, hepatovirus, cardioviruses, apthovirus, hepatitis A and other picornaviruses not yet assigned to a particular genus, including one or more of the serotypes of these viruses. Preferably the invention is used in the prevention or treatment of infection caused by one or more serotypes of rhinovirus.

Accordingly in a further aspect the present invention provides a method for the treatment of picornavirus infection including the step of administering an effective amount of a compound capable of binding to a picornavirus capsid comprising two or more capsid binding moieties.

While not wishing to be limited by theory, it is believed that the compounds according to the present invention act by stabilizing the capsid to an extent that prevents or reduces transmission from one host cell to another, or by interfering with the capsid/receptor interaction to a greater extent than the known capsid compounds. It is believed that through the co-operative binding of these multivalent capsid binding entities to the rhinovirus capsid which contains multiple capsid binding sites, that the overall anti-rhinovirus activity of the compounds of the invention is superior to the corresponding monomeric capsid binding compounds. Another possible method by which the multivalent capsid binding entities may act is by binding two or more viral capsids together, the subsequent aggregation of viruses reducing its infectivity. It is also believed that the binding of one capsid binding moiety within a capsid may result in an effective increase in localised concentration of binding moieties near the surface of the capsid and that this may contribute towards the increased binding affinity of the multivalent capsid binding compounds of the invention.

The invention also provides the use of a compound capable of binding to a picornavirus capsid comprising two or more capsid moieties in the manufacture of a medicament for the treatment of picornavirus infection.

While it is possible that, for use in therapy, a compound of the invention may be administered as the neat chemical, it is preferable to present the active ingredient as a pharmaceutical formulation.

In view of the general lipophilic nature of the compounds they are particularly suitable to oral forms of administration, however other forms of administration are also envisaged.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be acceptable" in the sense of being compatible with the other ingredients of the formulation and not deleterious to the recipient thereof.

The compounds of this invention may also be useful in combination with known anti-viral or anti-retroviral agents or other pharmaceuticals used in the treatment of viral infections. Representative examples of these additional pharmaceuticals include immunomodulators, immunostimulants, and antibiotics. Exemplary anti-viral agents include zanamivir, rimantidine, amantidine, ribavirin, AZT, 3TC, (–) FTC, acyclovir, famciclovir, penciclovir, ddI, ddC, ganciclovir, saquanivir, loviride, other non-nucleotide reverse transcriptase (RT) inhibitors and protease inhibitors, antiviral and antireceptor antibodies and receptor analogues, such as ICAM-1. Exemplary immunomodulators and immunostimulants include various interleukins, cytokines and antibody preparations. Exemplary antibiotics includes antifungal agents and antibacterial agents. Exemplary anti-inflammatory agents include glucocorticoids and non-steroidal anti-inflammatory compounds.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms. The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Liquids or powders for intranasal administration, tablets or capsules for oral administration and liquids for intravenous administration are preferred compositions.

The invention will now be described with reference to the following examples which illustrate some preferred aspects of the present invention, however it is to be understood that the particularity of the following description is not be supersede the generality of the invention described.

EXAMPLES

Example 1

Preparation of 3-(1-azido-3,6,9,12-tetraoxamidecyl)-5-[5-[2,6-dichloro-4-(4,5-dihydro-2-oxazolyl)phenoxy]-pentyl]-isoxazole (Compound 1)

3-(Hydroxymethyl)-5-[5-[2,6-dichloro-4-(4,5-dihydro-2-oxazolyl)phenoxy]-pentyl]-isoxazole (540 mg, 1.25 μmnol) in DCM (5 ml), prepared according to a literature procedure *J. Med. Chem*. (1990) 33, 1306-1311, was added rapidly to triphenylphosphine (410 mg, 1.56 mmol) and N-bromosuccinimide (278 mg, 1.56 mmol) in DCM (15 ml) at 0° C. The reaction was allowed to warm to room temperature, then after 3 hours the product was adsorbed onto silica gel and chromatographed on silica gel, eluent 1:1 ethyl acetate/hexane to give the brominated compound, 3-(bromomethyl)-5-[5-[2,6-dichloro-4-(4,5-dihydro-2-oxazolyl)phenoxy]-pentyl]-isoxazole as an off white solid (408 mg, 0.88 mmol) in 70% yield, Rf=0.25. $^1$H mm (D6 acetone): δ=8.01 (s, 2H); 6.46 (s, 1H); 4.69 (s, 2H); 4.61 (t, 2H); 4.26 (t, 2H); 4.16 (t, 2H); 3.00 (m, 2H); 2.2-1.7 ppm (m, 6H). MS (ES):$(M+H)^+$ 461,463,465. Neat 3,6,9-trioxa-11-azidoundecanol (237 mg, 1.08 mmol) prepared according to a literature procedure *J Org. Chem*. (1991) 56 4326, was added to a solution of sodium hydride (1.6 mmol) in DMF (3 ml) and stirred for 3 hours under argon. Tetrabutylammonium iodide (40 mg, 0.11 mmol) and a solution of the brominated compound (500 mg, 1.08 mmol) in DMF (3 ml) was added to the reaction. After 3 hours the reaction was quenched with water (1 ml) then partitioned between ethyl acetate (150 ml) and water (30 ml). The organic phase was washed with brine (30 ml), dried ($Na_2SO_4$) and concentrated to give a yellow brown oil. Chromatography of the crude residue twice on silica gel (50 g), eluent 2:1-3:1 ethyl acetate/hexane then 1:1 DCM/hexane gave 3-(1-azido-3,6,9,12-tetraoxamidecyl)-5-[5-[2,6-dichloro-4(4,5-dihydro-2-oxazolyl)phenoxy]-pentyl]-isoxazole (Compound 1) (400 mg, 0.67 mmol) in 62% yield. $^1$H nmr (D6 acetone): δ=8.01 (s, 2H); 6.34 (s, 1H); 4.70 (s, 2H); 4.61 (t, 2H); 4.26 (t, 2H); 4.16 (t, 2H); 3.8 (m, 14H); 3.52 (t, 2H); 2.95 (m, 2H); 2.2-1.7 ppm (m, 6H). MS (ES): $(M+H)^+$ 600.

Example 2

Preparation of 3-(1-amino-3,6,9,12-tetraoxamidecyl)-5-[5-[2,6-dichloro-4(4,5-dihydro-2-oxazolyl)phenoxy]-pentyl]-isoxazole (Compound 2) and 3-(1-(9-Fluorenylmethoxycarbonylamino)-3,6,9,12-tetraoxamidecyl)-5-[5-[2,6-dichloro-4(4,5-dihydro-2-oxazolyl)phenoxy]-pentyl]-isoxazole (Compound 3)

Triphenylphosphine (332 mg, 1.26 mmol) and water were added portionwise to a solution of Compound 1 (400 mg, 0.67 mmol) in THF (5 ml) over a period of 3 days whilst the reaction was stirred at room temperature under argon. The reaction was concentrated and the crude residue was chromatographed on Alumina (grade V basic, 40 g), eluent 1%-5% Methanol/DCM to give 3-(1-amino-3,6,9,12-tetraoxamidecyl)-5-[5-[2,6-dichloro-4(4,5-dihydro-2-oxazolyl)phenoxy]-pentyl]-isoxazole (Compound 2) (332 mg, 0.58 mmol) in 86% yield as a clear oil, Rf=0.4 in 5% Methanol/DCM: ninhydrin active. $^1$H nmr ($CD_3OD$): δ=7.91 (s, 2H); 6.27 (s, 1H); 4.61 (s, 2H); 4.55 (t, 2H); 4.12 (t, 2H); 4.07 (t, 2H); 3.7 (m, 12H); 3.54 (t, 2H); 2.87 (t, 2H); 2.80 (br, 1H); 2.0-1.6 ppm (m, 6H).N-hydroxysuccinimidyl 9-fluorenylmethoxycarbonate (141 mg, 0.42 mmol) was added to a solution of Compound 2 (210 μmol) and sodium bicarbonate (42 mg, 0.5 mmol) in dioxane/water (2:1, 12 ml). The reaction was allowed to stir overnight, then the reaction was concentrated and partitioned between ethyl acetate and water. Concentration and chromatography of the crude product on silica gel (20 g), eluent ethyl acetate, gave 3-(1-(9-Fluorenylmethoxycarbonylamino)-3,6,9,12-tetraoxamidecyl)-5-[5-[2,6-dichloro-4(4,5-dihydro-2-oxazolyl)phenoxy]-pentyl]-isoxazole (Compound 3) as a clear gum (110 mg, 0.138 mmol) in 66% yield. $^1$H nmr (D6 acetone): δ=8.01 (s, 2H); 7.99 (d, 2H); 7.84 (d, 2H); 7.55 (t, 2H); 7.47 (t, 2H); 6.68 (br, 1H); 6.35 (s, 1H); 4.67 (s, 2H); 4.60; 4.47 (d, 2H); 4.36 (m, 1H); 4.24 (t, 2H); 4.15 (t, 2H); 3.75 (m, 12H); 3.68 (t, 2H); 3.44 (m, 2H); 2.96 (t, 2H); 2.1-1.7 ppm (m, 6H). MS (ES): $(M+H)^+$ 796.

Example 3

3-(1-(Fmoc-triglycinylamido)-3,6,9,12-tetraoxamidecyl)-5-[5-[2,6-dichloro-4(4,5-dihydro-2-oxazolyl)phenoxy]-pentyl]-isoxazole (Compound 4)

A suspension of Fmoc-triglycine (9.7 mg, 24 μmol) in acetone (1 ml) containing triethylamine (3.5 μl, 24 μmol), N-methylmorpholine (1 μml, 1 μmol) and water (40 μl) was sonicated then cooled to −12° C. Isobutylchloroformate (4 μl, 28.5 μmol) was added and allowed to stir for 12 min, then a solution of Compound 2 (25 mmol) in acetone (1 ml) was added to the clear solution, followed by sodium bicarbonate (6 mg, 50 μmol) in water (250 μl). The reaction was stirred at 10° C. for 1.5 hours. The mixture was concentrated then adsorbed onto silica (1 g) and chromatography on silica gel (5 g) eluent 90:9:1 DCM:methanol:acetic acid gave 3-(1-(Fmoc-triglycinylamido)-3,6,9,12-tetraoxamidecyl)-5-[5-[2,6-dichloro-4(4,5-dihydro-2-oxazolyl)phenoxy]-pentyl]-isoxazole (Compound 4) (10 mg, 10 μmol) in 40% yield. $^1$H nmr ($CD_3OD$): δ=7.90 (s, 2H); 7.82 (m, 2H); 7.70 (m, 2H); 7.42 (m, 2H); 7.34 (m, 2H); 6.24 (s, 1H); 4.59 (s, 2H); 4.53 (t, 2H); 4.42 (d, 2H); 4.25 (m, 1H); 4.08 (t, 2H); 4.06 (t, 2H); 3.93 (s, 2H); 3.89 (s, 2H); 3.86 (s, 2H); 3.6 (m, 2H); 3.53 (t, 2H); 2.84 (t, 2H); 2.0-1.5 ppm (m, 6H). MS (ES): $(M+Na)^+$ 989.

Example 4

3-[1-(6-(6-Fmoc-caproamido)caproamido)-3,6,9,12-tetraoxamidecyl]-5-[5-[2,6-dichloro-4(4,5-dihydro-2-oxazolyl)phenoxy]-pentyl]-isoxazole (Compound 5)

Compound 5 was prepared in 20% yield from Compound 2 and 6-(6-Fmoc-caproamido)caproic acid following the procedure of the procedure of example 3. $^1$H nmr (D6 acetone): δ=8.01 (s, 2H); 8.0 (m, 2H); 7.55 (m, 2H); 7.46 (m, 2H); 6.37 (s, 1H); 4.69 (s, 2H); 4.60 (t, 2H) 4.46 (d, 2H); 4.36 (m, 1H); 4.25 (t, 2H); 4.15 (t, 2H); 3.8-3.7 (m, 2H); 3.62 (t, 2H); 3.46 (m, 2H); 3.3 (m, 4H); 2.95 (t,); 2.27 (m, 4H); 2.1-1.4 ppm (m, 8H). MS (ES): $(M+Na)^+$ 1044.

Example 5

Preparation of 3-(methoxymethyl)-5-[3-[2,6-dimethyl-4-phenylphenoxy]-propyl]-isoxazole (Compound 6) and 3-(1-hydroxy-3,6-dioxaheptyl)-5-[3-[2,6-dimethyl-4-phenylphenoxy]-propyl]-isoxazole (Compound 7).

T-butyllithium (1.3M in pentane, 17.9 ml, 23.2 mmol) was added slowly to a solution of 2,6-dimethyl-4-bromo-methoxybenzene (2.5 g, 11.6 mmol) in anhydrous THF (50 ml) at −78° C. under an atmosphere of argon, then after 1 hour a solution of anhydrous zinc chloride (1.6 g, 11.7 mmol) in THF (40 ml) was added by cannula and the clear solution allowed to warm to room temperature and stir for 1 hr. This solution was then added by cannula to iodobenzene (2.37 g, 11.6 mmol) and bis(triphenylphosphine)palladium (II)chloride (81 mg, 116 μmol) in THF (40 ml) and allowed to stir overnight. The reaction was added to 1N HCl (150 ml) and extracted into dichloromethane (2×300 ml). The organic phase was washed with water (150 ml), brine (150 ml) and dried ($Na_2SO_4$). The crude product was concentrated and purified by chromatography on silica gel (100 g), eluent 10% dichloromethanelhexanes to give 2,6-dimethyl-4-phenyl-methoxybenzene (2.11 g, 9.9 mmol) in 86% yield. $^1$H nmr ($CDCl_3$): δ=7.6-7.2 (m, 7H); 3.78 (s, 3H) and 2.37 (s, 6H). Boron tribromide (4.72 g, 19 mmol) was added dropwise to a solution of 2,6-dimethyl-4-phenyl-methoxybenzene (2.35 g, 11.1 mmol) in dichloromethane (45 ml) at −78° C. under argon, then the solution was allowed to warm to room temperature overnight. Ice/water (75 g) was added to quench the reaction, then the reaction was extracted with dichloromethane (2×200 ml). The organic layer was washed with water (50 ml), brine (50 ml) and dried ($Na_2SO_4$). Removal of the solvent gave 2,6-dimethyl-4-phenyl-phenol (2.15 g, 10.8 mmol) in 98% yield as a white solid, a single component by TLC Rf (0.13) eluent 4:1 dichloromethane/hexanes and $^1$H nmr. $^1$H nmr ($CDCl_3$): δ=7.6-7.2 (m, 7H); 4.70 (s, 1H) and 2.37 (m, 6H).

3-(Hydroxymethyl)-5-[3-[2,6-dimethyl-4-phenylphenoxy]-propyl]-isoxazole was prepared following procedures described in the literature; *J. Med. Chem.* (1994) 37 2421, thus 3-(t-butyldimethylsilyloxymethyl)-5-(3-hydroxypropyl)isoxazole (ibid.) and 2,6-dimethyl-4-phenyl-phenol were coupled by way of a Mitsunobu reaction to give the adduct, 3-(t-butyldimethylsilyloxymethyl)-5-[3-[2,6-dimethyl-4-phenylphenoxy]-propyl]-isoxazole in 82% yield. $^1$H nmr ($CDCl_3$): δ=7.6-7.2 (m, 7H); 6.13 (s, 1); 4.75 (d, 2H); 3.86 (t, 2H); 3.07 (t, 2H); 2.33 (s, 6H); 2.23 (m, 2H) and 2.1 (t, OH). MS (ES): (M+H) 338.1748 (calc. $C_{21}H_{24}NO_3$ 338.1750). Removal of the silyloxy group under acidic hydrolysis gave the hydroxy compound, 3-(hydroxymethyl)-5-[3-[2,6-dimethyl-4-phenylphenoxy]-propyl]-isoxazole in 93% yield. $^1$H mm ($CDCl_3$): δ=7.6-7.2 (m, 7H); 6.13 (s, 1H); 4.75 (d, 2H); 3.86 (t, 2H); 3.07 (t, 2H); 2.33 (s, 6H); 2.23 (m, 2H) and 2.1 (t, OH). MS (ES): (M+H) 338.1748 (calc. $C_{21}H_{24}NO_3$ 338.1750). Bromination of the hydroxy compound following the procedure of example 1 gave the bromomethyl compound, 3-(bromomethyl)-5-[3-[2,6-dimethyl-4-phenylphenoxy]-propyl]-isoxazole in 95% yield. $^1$H nmr ($CDCl_3$): δ=7.6-7.2 (m, 7H); 6.17 (s, 1H); 4.41 (s, 2H); 3.86 (t, 2H); 3.07 (t, 2H); 2.33 (s, 6H) and 2.23 (m, 2H). MS(ES): $(M+Na)^+$ 422.0725 (calc. $C_{21}H_{22}BrNO_2Na$ 422.0720).

Sodium hydride (9 mg, 0.22 mmol) was added to a solution of the hydroxy compound (50 mg, 0.15 mmol) in THF (3 ml) at 0° C. then the reaction was allowed to warm to room temperature and stirred for 1 hour under argon. Methyl iodide (105 mg, 0.74 mmol) was added and reaction was stirred overnight. Water (1 ml) was added and the reaction was partitioned between ethyl acetate (50 ml) and water (10 ml); the organic phase was washed with brine, dried ($Na_2SO_4$) and concentrated. Chromatography of the crude product on silica gel (10 g) eluent 85:15 hexane/ethyl acetate gave 3-(methoxymethyl)-5-[3-[2,6-dimethyl-4-phenylphenoxy]-propyl]-isoxazole (Compound 6) in 100% yield. $^1$H nmr ($CDCl_3$): δ=7.6-7.2 (m, 7H); 6.12 (s, 1H); 4.51 (s, 2H); 3.87 (t, 2H); 3.40 (s, 3H); 3.07 (t, 2H); 2.33 (s, 6H) and 2.25 (m, 2H). MS (ES): $(M+Na)^+$ 374.

After stirring a mix of sodium hydride (60% in oil, 7.5 mg, 187 μmmol) and diethylene glycol (45 mg, 425 μmol) in THF (2 ml) under argon for 1 hour, tetrabutylammonium iodide (5 mg) and a solution of the bromomethyl compound (75 mg, 187 μmol) in THF (1.5 ml) were added and the reaction was allowed to stir overnight. After addition of saturated ammonium chloride (1 ml) the reaction was partitioned between ethyl acetate (50 ml) and water (10 ml). The organic phase was washed with brine (15 ml), dried ($Na_2SO_4$) then concentrated to give a pale yellow oil. The crude product was chromatographed on silica gel (12 g), eluent 1:1 ethyl acetate/hexanes to give 3-(1-hydroxy-3,6-dioxaheptyl)-5-[3-[2,6-dimethyl-4-phenylphenoxy]-propyl]-isoxazole (Compound 7) (72 mg, 0.15 mmol) in 61% yield. $^1$H nmr ($CDCl_3$): δ=7.6-7.2 (m, 7H); 6.15 (s, 1H); 4.64 (s, 2H); 3.86 (t, 2H); 3.8-3.6 (m, 8H); 3.07 (t, 2H); 2.33 (s, 6H) and 2.23 (m, 2H). MS(ES): $(M+Na)^+$ 448.2082 (Calc. $C_{25}H_{31}NO_5Na$=492.2347).

Example 6

Preparation of Compound Nos. 8 to 13 (Table 2)

Compounds 8, 9, 10, 11, 12 and 13 were prepared from the bromomethyl compound described in example 5 and appropriate glycols using essentially the same method as described in example 5 for Compound 7. The compounds were purified on silica gel and characterised by their nuclear magnetic resonance (nmr) spectra and mass spectral (MS) data. The nmr and MS data are recorded in Table 4 below.

Example 7

Preparation of 3-(1-amino-3,6-dioxaheptyl)-5-[3-[2,6-dimethyl-4-phenylphenoxy]-propyl]-isoxazole (Compound 14).

Reaction of the bromomethyl compound of example 5 with 5-t-butyloxycarbonylamino-3-oxapentanol using essentially the same method as described in example 5 for Compound 7 gave the adduct, 3-(1-t-butyloxycarbonylamino-3,6-dioxaheptyl)-5-[3-[2,6-dimethyl-4-phenylphenoxy]-propyl]-isoxazole in 91% yield. Trifluoroacetic acid (1 ml) was added to a solution of the adduct (240 mg, 0.46 mmol) in DCM (10 ml) and the reaction was allowed to stir under argon for 2 hours. The reaction was concentrated at vacuum then the crude product was partitioned between brine/sodium bicarbonate (1:1, 20 ml) and ethyl acetate (2×100 ml). The combined organic phase was dried ($Na_2SO_4$) and concentrated, the crude product was chromatographed on silica gel (20 g); eluent 92.5:7.5 DCM/(10% ammonia in methanol) to give 3-(1-amino-3,6-dioxaheptyl)-5-[3-[2,6-dimethyl-4-phenylphenoxy]-propyl]-isoxazole (Compound 14) in 71% yield. $^1$ H nmr ($CD_3OD$): δ=7.5-7.15 (m, 7H); 6.24 (s, 1H); 4.55 (s, 2H); 3.81 (t, 2H); 3.61 (s, 4H); 3.46 (t, 2H); 3.03 (t, 2H); 2.72 (t, 2H); 2.26 (s, 6H) and 2.16 (m, 2H). MS (ES): $(M+H)^+$ 425.2428 (Calc. $C_{25}H_{32}N_2O_4H$=425.2432).

Example 8

Preparation of Compound Nos. 15 to 17 (Table 2)

Compounds 15, 16 and 17 were prepared from the bromomethyl compound of example 5 and appropriate t-Boc-glycols using essentially the same method as described in example 7 for Compound 14. The compounds were purified on silica gel and characterised by their nuclear magnetic resonance (nmr) spectra and mass spectral (MS) data. The mm and MS data are recorded in Table 4 below.

Example 9

3-[1-(1-amino-3,6,9,12,15,18-hexaoxanonadecyl)-4-(2,5,8,11,14,17,20-heptaoxaheneicosyl)-phenyl]-5-[3-[2,6-dimethyl-4-phenylphenoxy]-propyl]-isoxazole (Compound 18)

A THF solution of sodium hexamethyldisilazide (1M, 0.54 ml, 0.54 mmol) was added to 17-t-butyloxycarbonylamino-3,6,9,12,15-pentaoxaheptadecanol (189 mg, 0.49 mmol) in THF (5 ml), then after 45 min stirring at room temperature the mixture was added slowly to a solution of dibromo-p-xylene (388 mg, 1.47 mmol) in THF (5 ml). The reaction was stirred overnight then quenched with saturated ammonium chloride (1 ml) and partitioned between ethyl acetate (100 ml) and water (20 ml). The organic phase was washed with brine, dried ($Na_2SO_4$) and concentrated. The crude product was chromatographed on silica gel (20 g); eluent 98:2 DCM/methanol, to give the benzyl bromide, 4-(1 t-butyloxycarbonylamino-3,6,9,12,15,18-hexaoxanonadecyl)-benzyl bromide in 60% yield. $^1$H nmr ($CDCl_3$): δ=7.35 (m, 4H); 4.55 (s, 2H); 4.49 (s, 2H); 3.7-3.5 (m, 22H); 3.29 (t, 2H) and 1.43 (s, 9H). A THF solution of sodium hexamethyldisilazide (1M, 0.36 ml, 0.36 mmol) was added to Compound 10 (172 mg, 0.29 mmol) in THF (3 ml) then after 45 min stirring at room temperature, tetrabutylammonium iodide (10 mg) and a solution of the benzyl bromide (165 mg, 0.29 mmol) in THF (3 ml) were added and the reaction was stirred overnight under argon. The reaction was quenched with saturated ammonium chloride and partitioned between ethyl acetate (100 ml) and water (20 ml). The organic phase was washed with brine, dried ($Na_2SO_4$) and concentrated. The crude product was chromatographed on silica gel (20 g); eluent 97.5:2.5 DCM/methanol to give a mix of 2 components. Trifluoroacetic acid (1 ml) was added to a solution of this mixture in DCM (10 ml) and the reaction was stirred under argon for 1 hour. The solvents were removed under vacuum and the crude residue was basified with saturated sodium bicarbonate (20 ml) and extracted into ethyl acetate (2×50 ml). The combined organic phases were washed with brine, dried ($Na_2SO_4$) and concentrated. The crude product was chromatographed on alumina (grade V, 30 g); eluent 98:2 DCM/methanol, to give 3-[1-(1-amino-3,6,9,12,15,18-hexaoxanonadecyl)-4-(2,5,8,11,14,17,20-heptaoxaheneicosyl)-phenyl]-5-[3-[2,6-dimethyl-4-phenylphenoxy]propyl]-isoxazole (Compound 18) (74 mg, 75 μmol). $^1$H nmr ($CD_3OD$): δ=7.65-7.25 (m, 11H); 6.34 (s, 1H); 4.62 (s, 2H); 4.56 (s, 4H); 3.89 (t, 2H); 3.75-3.55 (m, 44H); 3.53 (t, 2H); 3.11 (t, 2H); 2.80 (t, 2H); 2.34 (s, 6H) and 2.24 (m, 2H).

Example 10

3-(1-acetamido-3,6-dioxaheptyl)-5-[3-[2,6-dimethyl-4-phenylphenoxy]-propyl]-isoxazole (Compound 19)

Acetic anhydride (67 mg, 0.66 mmol) was added to a solution of Compound 14 (28 mg, 66 μmol) in pyridine (1.5 ml) and the reaction was allowed to stir over 4 days under argon. The solvents were removed under vacuum and the crude residue was chromatographed on silica gel (10 g); eluent 96:4 DCM/methanol, to give 3-(1-acetamido-3,6-dioxaheptyl)-5-[3-[2,6-dimethyl-4-phenylphenoxy]-propyl]-isoxazole (Compound 19) (27 mg, 58 μmol) in 88% yield. $^1$H nmr ($CDCl_3$): δ=7.6-7.2 (m, 7H); 6.13 (s, 1H); 4.64 (s, 2H); 3.87 (t, 2H); 3.65 (s, 4H); 3.56 (m, 2H); 3.03 (t, 2H); 2.72 (t, 2H); 2.26 (s, 6H) and 2.16 (m, 2H). MS (ES): $(M+Na)^+$ 489.2388 (Calc. $C_{27}H_{34}N_2O_5Na$=489.2351).

Example 11

Preparation of Compound Nos. 20 to 22 (Table 2)

Compounds 20, 21 and 22 were prepared from Compounds 15, 16 and 17 respectively, using essentially the same method as described in example 10 for Compound 19. The compounds were purified on silica gel and characterised by their nuclear magnetic resonance (mm) spectra and mass spectral (MS) data. The nmr and MS data are recorded in Table 4 below.

Example 12

Preparation of 3-(1-hydroxy-3,6-dioxaheptyl)-5-[3-[2,6-dimethyl-4-(5-trifluoromethyl-1,2,4-oxadiazolyl)phenoxy]-propyl]-isoxazole (Compound 23).

Bromination of 3-(hydroxymethyl)-5-[3-[2,6-dimethyl-4-(5-trifluoromethyl-1,2,4-oxadiazolyl)phenoxy]-propyl]-isoxazole (prepared following a literature procedure; *J. Med. Chem*. (1995) 38 1355), following example 1 gave the bromomethyl compound, 3-(bromomethyl)-5-[3-[2,6-dimethyl-4-(5-trifluoromethyl-1,2,4-oxadiazolyl)phenoxy]-propyl]-isoxazole in 95% yield. $^1H$ nmr ($CDCl_3$): δ=7.78 (s, 2H); 6.17 (s, 1H); 4.41 (s, 2H); 3.88 (t, 2H); 3.06 (t, 2H); 2.33 (s, 6H) and 2.24 (m, 2H). Added a THF solution of sodium hexamethyldisilazide (1M, 0.54 ml, 0.54 mmol) to diethylene glycol (91 mg, 0.86 mmol) in THF (7 ml). The suspension was stirred for 1 hour then tetrabutylammonium iodide (20 mg) and a solution of the bromomethyl compound (200 mg, 0.43 mmol) in THF (3 ml) were added and the reaction was allowed to stir overnight. The reaction was quenched with saturated ammonium chloride (1 ml) and partitioned between ethyl acetate (100 ml) and water (20 ml). The organic layer was washed with brine, dried ($Na_2SO_4$) and concentrated. The crude product was chromatographed on silica gel (20 g); eluent 97.5:2.5 DCM/methanol to give 3-(1-hydroxy-3,6-dioxaheptyl)-5-[3-[2,6-dimethyl-4-(5-trifluoromethyl-1,2,4-oxadiazolyl)phenoxy]-propyl]-isoxazole (Compound 23) (55 mg, 0.1 lImmol) in 26% yield and 95% purity by $^{19}F$ mnr. $^1H$ mmr ($CDCl_3$): δ=7.78 (s, 2H); 6.15 (s, 1H); 4.63 (s, 2H); 3.88 (t, 2H); 3.8-3.6 (m, 8H); 3.06 (t, 2H); 2.33 (s, 6H) and 2.23 (m, 2H). $^{19}F$ nmr ($CDCl_3$): δ=−65.9 (95%); −76.0 (5%). MS (ES): $(M+H)^+$ 486.1844 (Calc. $C_{22}H_{26}N_3O_6F_3H$=486.1845).

Example 13

Preparation of Compound Nos. 24 to 26 (Table 2)

Compounds 24, 25 and 26 were prepared from the bromomethyl compound of example 12 and appropriate glycols using essentially the same method as described in example 12 for Compound 23. The compounds were purified on silica gel and characterised by their nuclear magnetic resonance (nmr) spectra and mass spectral (MS) data. The mm and MS data are recorded in Table 4 below.

Example 14

Preparation of 2-[4(2,5-dimethylbenzyl)-piperazine-1-yl]-4-[(1-t-butyloxycarbonylamino-3,6-dioxaoctanyl)-aminocarbonyl]-thiazole (Compound 27) and 2-[4(2,5-dimethylbenzyl)-piperazin-1-yl]-4-[(8-amino-3,6-dioxa-octan-1-yl)-amino-carbonyl]-thiazole (Compound 28)

(i) Preparation of 2-[4-(2,5-dimethylbenzyl)-piperazine-1-yl]-4-[(1-t-butyloxycarbonylamino-3,6-dioxaoctanyl)-aminocarbonyl]-thiazole (Compound 27)

To a solution of 2-[4-(2,5-dimethylbenzyl)-piperazin-1-yl]-thiazole-4-carboxylic acid triethylamine salt (D. A. Oren, et al., J. Mol. Biol., 259, 120 (1996) and German Patent 2,726,513, Chemical Abstracts 90, 104016j (1979)) (194.2 mg, 0.449 mmol) in a mixture of acetone (1.8 ml) and water (0.6 ml) at −20° C. were added successively N-methylmorpholine (45 mg, 0.445 mmol), and isobutyl chloroformate (73.5 mg, 0.539 mmol). The whole mixture was stirred at −15-20° C. for 15 min. before combining with a solution of 1-amino-3,6-dioxa-8-t-butoxycarbonylamino-octane (112 mg, 0.450 mmol) in 50% aqueous acetone (2.4 ml). The resulting reaction mixture was then stirred at room temperature for 3 hrs, evaporated in vacuum to dryness. The residue was partitioned between dichloromethane (30 ml) and 5% $NaHCO_3$ solution (10 ml). The organic layer was then washed with water (10 ml×3), dried over anhydrous $Na_2SO_4$, evaporated to dryness. The residue was then dissolved in ether, diluted with hexane to afford 2-[4-(2,5-dimethylbenzyl)-piperazine-1-yl]-4-[(1-t-butyloxycarbonylamino-3,6-dioxaoctanyl)-aminocarbonyl]-thiazole (Compound 27) (190 mg, 75%). 1H-nmr ($CD_3OD$) δ (ppm) 1.45 (s, 9H), 2.25 (s, 3H), 2.31 (s, 3H), 2.58 (br.t, 4H), 3.10~3.70 (m, 18H), 7.01 (m, 3H), 7.35 (s, 1H). MS (ESI) 562 $(M+1)^+$ (ii) Preparation of 2-[4-(2,5-dimethylbenzyl)-piperazin-1-yl][(8-amino-3,6-dioxa-octan-1-yl)-amino-carbonyl]-thiazole (Compound 28)

Compound 27 (100 mg, 0.178 mmol) was treated with trifluoroacetic acid (2 ml) under argon at room temperature for 1 hr, then evaporated into dryness. The residue was partitioned between ether (50 ml) and 5% $Na_2CO_3$ solution (10 ml).

The organic layer was washed with water (10 ml×3), dried over anhydrous $Na_2SO_4$, evaporated in vacuum to afford 2-[4-(2,5-dimethylbenzyl)-piperazin-1-yl]-4-[(8-amino-3,6-dioxa-octan-1-yl)-amino-carbonyl]-thiazole (Compound 28) (70 mg, 85%). 1H-nmr ($CD_3OD$) δ (ppm) 2.26 (s, 3H), 2.32 (s, 3H), 2.55 (br.t, 4H), 2.75 (br.t, 2H) 3.35-3.68 (m, 16H), 7.02 (m, 3H), 7.35 (s, 1H). MS (ESI) 462 $(M+1)^+$

Example 15

Preparation of 2-[4(2,5-dimethylbenzyl)-piperazin-1-yl]-4-[(12-amino-4,9-dioxa-dodecan-1-yl)-amino-carbonyl]-thiazole (Compound 29)

According to the procedure described in Example 14, Compound 29 (30 mg, 61%) was obtained from the 2-[4'-(2",5"-dimethylbenzyl)-piperazin-1'-yl]-thiazole-4-carboxylic acid triethylamine salt (40.6 mg, 0.094 mmol) and 1-amino-4,9-dioxa-12-t-butoxycarbonylamino-dodecane (30 mg, 0.098 mmol). $^1H$nmr ($CD_3OD$) δ (ppm) 1.51~1.81 (m, 8H), 2.32 (s, 3H), 2.38 (s, 3H), 2.52 (br.t, 4H), 2.78 (t, 2H), 3.11-3.86 (m, 16H), 7.02 (m, 3H), 7.35 (s, 1H). MS (ESI) 518 $(M+1)^+$.

Example 16

Preparation of 4-(t-butoxycarbonylaminoacetylamino)-benzyl 2-[1(2,5-dimethylbenzyl)-piperazin-1-yl]-thiazole-4-carboxylate (Compound 30)

To a solution of 2-[4'-(2",5"-dimethylbenzyl)-piperazin-1'-yl]-thiazole-4-carboxylic acid triethylamine salt (64 mg, 0.148 mmol) in acetone (5 ml), was added trifluoroacetic acid to adjust to pH 1~2. The solution was stirred at room temperature for 1 min. before being evaporated under reduced pressure to dryness. The residue was then dissolved in DMF (2 ml) containing 1,3-dicyclohexylcarbodiimide (34 mg, 0.164 mmol), 4-dimethylaminopyridine (2 mg, 0.0164 mmol), and 4-(t-butoxycarbonylaminoacetylamino)-benzyl alcohol (53.7 mg, 0.156 mmol). The mixture was stirred under argon at room temperature for 16 hrs., then diluted with dichloromethane (10 ml), filtered off. The filtrate was evaporated under reduced pressure to dryness. The residue was partitioned between ethyl ether (40 ml) and 5% $NaHCO_3$ solution (10 ml). The ethyl ether extract was washed with water (10 ml×2), dried over anhydrous $Na_2SO_4$, and evaporated into dryness. The residue was allowed to dissolve in ethyl acetate (1 ml), then left at refrigerator overnight. The crystals were collected by filtration to afford 4'''-(t-butoxycarbonylaminoacetylamino)-benzyl 2-[4'-(2'',5''-dimethylbenzyl)-piperazin-1'-yl]-thiazole-4-carboxylate (Compound 30) (23 mg, 26%). $^1$H-nmr ($CD_3OD$) δ (ppm) 1.49(s, 9H), 2.28 (s, 3H), 2.34 (s, 3H), 2.52 (br., 4H), 3.32~3.92 (m, 8H), 4.81 (br., 2H), 6.95~7.60 (m, 8H). MS (ESI) 594 $(M+1)^+$.

Example 17

Preparation of α-ω-bis-[5-[5-[2,6-dichloro-4(4,5-dihydro-2-oxazolyl)phenoxy]-pentyl]-isoxazolyl-3-methoxy-(3,6,9-trioxaundecyl-11-amidomethoxy)]-polyethyleneglycol ($MW_{av}$600) (Compound 31)

Isobutylchloroformate (10 μl, 74,umol) was added to a solution of α-ω-bis-(carboxymethoxy)-polyethyleneglycol ($MW_{av}$ 600; 19 mg, 31 μmol), water (40 μl), triethylamine (9 μl, 62 μmol) and N-methylmorpholine (1 μl, 10 μmol) in acetone (1 ml) at −12° C. and stirred for 12 min. A solution of Compound 2 (69 μmol) in acetone (1.5 ml) and sodium bicarbonate (7 mg, 83 μmol) in water (200 μl) were added to the reaction then it was allowed to warm slowly from 10° C. to room temperature overnight. The reaction mix was adsorbed onto silica gel (1 g) and chromatographed on silica gel (10 g) eluent 90:9:1 DCM/methanol/acetic acid to give α-ω-bis-[5-[5-[2,6-dichloro-4(4,5-dihydro-2-oxazolyl)phenoxy]-pentyl]-isoxazolyl-3-(2,5,8,11-tetraoxamidecylamidomethoxy)]-polyethyleneglycol ($MW_{av}$600) (Compound 31) (20 mg, 12 μmol) in 34% yield. $^1$H nmr ($CD_3OD$): δ=7.9 (s, 4H); 6.3 (s, 2H); 4.65 (s, 4H), 4.55 (t, 4H); 4.15 (t, 4H); 4.05 (t, 4H); 4.0 (s, 4H); 3.7 (m, 60H); 3.95 (m, 4H); 2.85 (t, 4H); 2.0-1.6 ppm (m). MS (ES): $(M+Na: Peg_{n=8})^+$1622.

Example 18

Preparation of 1,8-bis-[5-[3-[2,6-dimethyl-4-phenylphenoxy]-propyl]-isoxazolyl-3-methyloxy]-3,6-dioxaoctane (Compound 32)

Sodium hydride (60% in oil, 4 mg, 0.93 μmol) was added to a solution of Compound 8 (35 mg, 75 μmol) in THF (2 ml) then after stirring reaction under argon for 1 hour, tetrabutylammonium iodide (10 mg) and a solution of the bromomethyl compound of Example 5 (30 mg, 75 μmol) in THF (1.5 ml) were added and the reaction was allowed to stir overnight. After addition of saturated ammonium chloride (1 ml) the reaction was partitioned between ethyl acetate (50 ml) and water (15 ml). The organic phase was washed with brine, dried ($Na_2SO_4$) then concentrated to give a pale yellow oil. The crude product was chromatographed on silica gel (10 g), eluent 1:1 ethyl acetate/hexanes to give 1,8-bis-[5-[3-[2,6-dimethyl-4-phenylphenoxy]-propyl]-isoxazolyl-3-methyloxy]-3,6-dioxaoctane (Compound 32) (21 mg, 27 μmol) as a clear oil in 35% yield. $^1$H nmr ($CDCl_3$): δ=7.6-7.2 (m, 14H); 6.14 (s, 2H); 4.61 (s, 4H); 3.86 (t, 4H); 3.67 (s, 12H); 3.06 (t, 4H); 2.32 (s, 12H) and 2.22 (m, 4H). MS (ES): $(M+Na)^+$ 811.3947 (Calc. $C_{48}H_{56}N_2O_8Na$=811.3911).

Example 19

Preparation of Compound Nos. 33,34,35,36 and 37 (Table 3)

Compounds 33, 34, 35, 36 and 37 were prepared from Compounds 9, 10, 11, 12 and 13 and the bromomethyl compound of Example 5 using essentially the same method as described in example 17 for Compound 32. The compounds were purified on silica gel and characterised by their nuclear magnetic resonance (nmr) spectra and mass spectral (MS) data. The nmr and MS data are recorded in Table 4 below.

Example 20

Preparation of 1,4-bis-[5-[3-[2,6-dimethyl-4-phenylphenoxy]-propyl]-isoxazolyl-3-(2,5,8-trioxanonyl)]-benzene (Compound 38)

Sodium hydride (60% in oil, 5 mg, 123 μmol) was added to a solution of Compound 7 (35 mg, 82 μmol) in THF (2 ml), then after 1 hour stirring under argon tetrabutylammonium iodide (10 mg) and dibromo-p-xylene (10.5 mg, 41 μmol) were added and the reaction was allowed to stir overnight. The reaction was quenched with saturated ammonium chloride then partitioned between ethyl acetate (50 ml) and water (10 ml). The organic phase was washed with brine, dried ($Na_2SO_4$) and concentrated. Chromatography of the crude residue on silica gel (12 g); eluent 98.5:1.5 DCM/methanol, gave 1,4-bis-[5-[3-[2,6-dimethyl-4-phenylphenoxy]-propyl]-isoxazolyl-3-(2,5,8-trioxanonyl)]-benzene (Compound 38) (19 mg, 20 mmol) in 48% yield. $^1$H nmr ($CDCl_3$): δ=7.6-7.2 (m, 18H); 6.14 (s, 2H); 4.62 (s, 4H); 4.55 (s, 4H); 3.85 (t, 4H); 3.7-3.55 (m, 16H); 3.05 (t, 4H); 2.32 (s, 12H) and 2.21 (m, 4H). MS(ES): $(M+Na)^+$ 975.4772 (Calc. $C_{58}H_{68}N_2O_{10}Na$ 975.4748).

Example 21

Preparation of Compounds 39,40 and 41 (Table 3)

Compounds 39, 40 and 41 were prepared from Compounds 8, 9 and 10 using essentially the same method as described in example 20 for Compound 38. The compounds were purified on silica gel and characterised by their nuclear magnetic resonance (mnr) spectra and mass spectral (MS) data. The nmr and MS data are recorded in Table 4 below.

Example 22

Preparation of 1,3-bis-[5-[3-[2,6-dimethyl-4-phenylphenoxy]-propyl]-isoxazolyl-3-methoxy-(3-oxapentyl-5-aminocarbonylamino)]-6-methylbenzene (Compound 42)

Added toluene-2,4-diisocyanate (8 mg, 46 μmol) to a solution of Compound 14 (43 mg, 101 μmol) in DMF (1.5 ml) containing triethylamine (10 mg, 10 μmol) then the reaction was allowed to stir under argon for 4 days. The reaction was adsorbed onto silica gel (1 g) and chromatographed on silica gel (10 g); eluent 96:4 DCM/methanol, to give 1,5-bis-[5-[3-[2,6-dimethyl-4-phenylphenoxy]-propyl]-isoxazolyl-3-methoxy-(3-oxapentyl-5-aminocarbonylamino)]-6-methylbenzene (Compound 42) (38 mg, 37 μmol) in 73% yield. $^1$H nmr ($CDCl_3$): δ=7.6-7.2 (m, 17H); 6.12 (s, 1H); 6.10 (s, 1H); 4.63 (s, 2H); 4.59 (s, 2H); 3.85 (m, 4H); 3.7-3.5 (m, 12H); 3.42 (m, 4H); 3.05 (m, 4H); 2.31 (s, 12H); 2.21 (m, 4H) and 2.13 (s, 3H). MS (ES): $(M+Na)^+$ 1045.5100 (Calc. $C_{59}H_{70}N_6O_{10}Na$=1045.5028).

Example 23

Preparation of Compounds 43, 44, 45, 46, 47, 48 and 49 (Table 3)

Compounds 43, 44 and 45 were prepared from Compounds 15, 16 and 17 using essentially the same method as described in example 22 for Compound 42, and using similar methodology reaction of Compounds 14, 15, 16 and 17 with 4,4'-methylenebis(phenyl isocyanate) gave Compounds 46, 47, 48 and 49. The compounds were purified on silica gel and characterised by their nuclear magnetic resonance (nmr) spectra and mass spectral (MS) data. The nmr and MS data are recorded in Table 4 below.

Example 24

Preparation of 1,5-bis-[5-[3-[2,6-dimethyl-4-(5-trifluoromethyl-1,2,4-oxadiazolyl)phenoxy]-propyl]-isoxazolyl-3-methyloxy]-3-oxapentane (Compound 50)

(i) Preparation of 3-(bromomethyl)-5-(3-t-butyldiphenylsilyloxypropyl)isoxazole

T-butyldiphenylsilyl chloride (6.0 g, 22 mmol) was added to a solution of 3-(t-butyldimethylsilyloxymethyl)-5-(3-hydroxypropyl)isoxazole (4.74 g, 17.5 mmol), imidazole (1.55 g, 22.7 mmol) in anhydrous DMF (5 ml) then the reaction was stirred overnight under argon. The reaction was concentrated then taken up in hexanes (300 ml) and washed with water (3×50 ml) and brine. The organic phase was dried ($Na_2SO_4$) and concentrated then chromatographed on silica gel (300 g); eluent 97:3 hexanes/ethyl acetate, to give 3-(t-butyldimethylsilyloxymethyl)-5-(3-t-butyldiphenylsilyloxypropyl)isoxazole (8.3 g, 16.3 mmol) in 93% yield. H nrnr ($CDCl_3$): δ=7.66 (m, 4H); 7.42 (m, 6H); 6.00 (s, 1H); 4.72 (s, 2H); 3.71 (t, 2H); 2.88 (t, 2H); 1.94 (m, 2H); 1.06 (s, 9H); 0.92 (s, 9H) and 0.10 (s, 6H). M.S. (M+H) 510.2887 (Calc. $C_{29}H_{43}NO_3Si_2H$=510.2848). Removal of the silyloxy group under acidic hydrolysis following example 5 gave 3-(hydroxymethyl)-5-(3-t-butyldiphenylsilyloxypropyl)isoxazole in 91% yield. $^1$H nmr ($CDCl_3$): δ=7.65 (m, 4H); 7.42 (m, 6H); 5.96 (s, 1H); 4.70 (s, 2H); 3.71 (t, 2H); 2.88 (t, 2H); 1.94 (m, 2H) and 1.06 (s, 9H). M.S. $(M+H)^+$ 396.2009 (Calc. $C_{23}H_{29}NO_3SiH$=396.1987). Bromination following example 1 gave the bromomethyl compound 3-(bromomethyl)-5-(3-t-butyldiphenylsilyloxypropyl)isoxazole in 75% yield. $^1$H nmr ($CDCl_3$): δ=7.66 (m, 4H); 7.42 (m, 6H); 6.00 (s, 1H); 4.37 (s, 2H); 3.71 (t, 2H); 2.89 (t, 2H); 1.94 (m, 2H) and 1.07 (s, 9H). M.S. (M+Na)+480.0959 (Calc. $C_{23}H_{28}NO_2BrSiNa$=480.0957).

(ii) Preparation of 3-(1-hydroxy-3,6-dioxaheptyl)-5-(3-t-butyldiphenylsilyloxypropyl]-isoxazole Reaction of the bromomethyl compound with diethylene glycol and sodium hydride in THF using essentially the same method as described in example 5 for Compound 7 gave 3-(1-hydroxy-3,6-dioxaheptyl)-5-(3-t-butyldiphenylsilyloxypropyl)]-isoxazole in 67% yield. $^1$H nmr ($CDCl_3$): δ=7.65 (m, 4H); 7.39 (m, 6H); 6.02 (s, 1H); 4.60 (s, 2H); 3.67 (m, 10H); 2.89 (t, 2H); 1.94 (m, 2H) and 1.06 (s, 9H). M.S. $(M+Na)^+$ 506.2343 (Calc. $C_{27}H_{37}NO_5SiNa$=506.2329).

(iii) Preparation of 1,5-bis-[5-[3-[2,6-dimethyl-4-(5-trifluoromethyl-1,2,4-oxadiazolyl)phenoxy]-propyl]-isoxazolyl-3-methyloxy]-3-oxapentane (Compound 50)

Sodium hydride (60% in oil, 16 mg, 0.39 mmol) was added to a solution of 3-(1-hydroxy-3,6-dioxaheptyl)-5-(3-t-butyldiphenylsilyloxypropyl]-isoxazole (ii) (127 mg, 0.26 mmol), tetrabutylammonium iodide (10 mg) and 3-(bromomethyl-5-(3-t-butyldiphenylsilyloxypropyl)isoxazole (120 mg, 0.26 mmol) in THF, then the reaction was allowed to stir overnight under argon. The reaction was quenched with saturated ammonium chloride then partitioned between ethyl acetate (3×25 ml) and brine (10 ml). The organic phase was dried ($Na_2SO_4$) and concentrated. Chromatography of the crude residue on silica gel (20 g); eluent 75:25 hexanes/ethyl acetate, gave 1,5-bis-[5-[3-(t-butyldiphenylsilyloxypropyl)]-isoxazolyl-3-methyloxy]-3-oxapentane (144 mg, 0.167 mmol) in 64% yield. $^1$H nmr ($CDCl_3$): δ=7.62 (m, 8H); 7.40 (m, 12H); 6.00 (s, 2H); 4.58 (s, 4H); 3.70 (t, 4H); 3.65 (s, 8H); 2.87 (t, 4H); 1.92 (m, 4H) and 1.05 (s, 18H). A THF solution of tetrabutylammonium fluoride (1M, 0.465 ml, 0.465 mmol) was added to a solution of the adduct (133 mg, 0.155 mmol) in THF (3 ml) and the reaction was stirred overnight under argon. The reaction was concentrated, then partitioned between brine (5 ml) and ethyl acetate (3×20 ml). The combined organic phases were dried ($Na_2SO_4$) and concentrated then chromatography of the crude residue on silica gel (7.5 g); eluent 96:4 DCM/methanol, gave bridging compound 1,5-bis-[5-[3-hydroxypropyl]-isoxazolyl-3-methyloxy]-3-oxapentane (57 mg, 0.148 mmol) in 96% yield. $^1$H nmr ($CDCl_3$): δ=6.09 (s, 2H); 4.57 (s, 4H); 3.67 (t, 4H); 3.64 (s, 8H); 2.84 (t, 4H) and 1.92 (m, 4H). Diisopropylazodicarboxylate (38 mg, 189 mmol) was added to an ice cold solution of the bridging compound (29 mg, 76 μmol), triphenylphosphine (50 mg, 189 μmol) and 2,6-dimethyl-4-(5-trifluoromethyl-1,2,4-oxadiazolyl)phenol (49 mg, 189 μmol) (prepared following a literature procedure; *J. Med. Chem.* (1995) 38 1355) in ether (1 ml) then the reaction was allowed to warm to room temperature and stirred overnight under argon. The reaction was filtered and concentrated then the crude residue was chromatographed on silica gel (10 g); eluent 2:1 hexanes/ethyl acetate, to give 1,5-bis-[5-[3-[2,6-dimethyl-4-(5-trifluoromethyl-1,2,4-oxadiazolyl)phenoxy]-propyl]-isoxazolyl-3-methyloxy]-3-oxapentane (Compound 50) (48 mg, 55 μmol) in 73% yield. $^1$H nmr (D6 acetone): δ=7.77 (s, 4H); 6.31 (s, 2H); 4.58 (s, 4H); 3.97 (t, 4H); 3.64 (s, 8H); 3.09 (t, 4H); 2.36 (s, 12H) and 2.25 (m, 4H). $^{19}$F nmr (D6 acetone): δ=65.5 ppm.

Example 25

Preparation of Compounds 51, 52 and 53 (Table 3)

Compounds 51, 52 and 53 were prepared using essentially the same method as described in example 24 for Compound 50 by using appropriate glycols in step (ii). The compounds were purified on silica gel and characterised by their nuclear magnetic resonance (mm) spectra and mass spectral data. The nmr and MS data are recorded in Table 4 below.

Example 26

Preparation of 1,4-bis-[5-[3-[2,6-dimethyl-4-(5-trifluoromethyl-1,2,4-oxadiazolyl)phenoxy]-propyl]-isoxazolyl-3-(2,5,8-trioxanonyl)]-benzene (Compound 54)

Sodium hydride (21 mg, 0.52 mmol) was added to a solution of the product of step (ii) of example 24 (169 mg, 0.35 mmol), dibromo-p-xylene (44 mg, 0.17 mmol) and tetrabutylammonium iodide (13 mg) and the reaction was left to stir overnight under argon. After addition of saturated ammonium chloride (1 ml) the reaction was partitioned between brine (10 ml) and ethyl acetate (2×50 ml). The combined organic phases were dried ($Na_2SO_4$) then concentrated. Chromatography of the crude residue on silica gel (2×15 g); eluents 3:2 hexanes/ethyl acetate then 98.5:1.5 DCM/methanol gave 1,4-bis-[5-[3-(t-butyldiphenylsilyloxypropyl)]-isoxazolyl-3-(2,5,8-trioxanonyl)]-benzene (86 mg, 80 μmol) in 46% yield. $^1$H nmr ($CDCl_3$): δ=7.65 (m, 8H); 7.40 (m, 12H); 7.30 (s, 4H); 6.01 (s, 2H); 4.59 (s, 4H); 4.54 (s, 4H); 3.70 (t, 4H); 3.7-3.55 (m, 16H); 2.87 (t, 4H); 1.92 (m, 4H) and 1.05 (s, 18H). M.S. (ES)(M+Na)$^+$ 1091.5187 (Calc. $C_{62}H_{80}N_2O_{10}Si_2Na$=1091.5228). A THF solution of tetrabutylammonium fluoride (1M, 225 μl, 225 μmol) was added to a solution of 1,4-bis-[5-[3-(t-butyldiphenylsilyloxypropyl)]-isoxazolyl-3-(2,5,8-trioxanonyl)]-benzene (80 mg, 75 μmol) in THF (3 ml). After stirring overnight under argon the reaction was concentrated and the residue chromatographed on silica gel (7.5 g); eluent 96:4 DCM/methanol, to give the bridging compound, 1,4-bis-[5-[3-(hydroxypropyl)]-isoxazolyl-3-(2,5,8-trioxanonyl)]-benzene 1,4-bis-[5-[3-(t-butyldiphenylsilyloxypropyl)]-isoxazolyl-3-(2,5,8-trioxanonyl)]-benzene (40 mg, 67 μmol) in 90% yield. $^1$H nmr ($CDCl_3$): δ=7.30 (s, 4H); 6.09 (s, 2H); 4.59 (s, 4H); 4.54 (s, 4H); 3.60 (m, 20H); 2.82 (t, 4H) and 1.90 (m, 4H). M.S. (ES) (M+Na)$^+$ 615.2920 (Calc. $C_{30}H_{44}N_2O_{10}Na$=615.2882). Reaction of the bridging compound with 2 equivalents of 2,6-dimethyl-4-(5-trifluoromethyl-1,2,4-oxadiazolyl)phenol using essentially the same method as described in example 24 for Compound 50 gave 1,4-bis-[5-[3-[2,6-dimethyl-4-(5-trifluoromethyl-1,2,4-oxadiazolyl)phenoxy]-propyl]-isoxazolyl-3-(2,5,8-trioxanonyl)]-benzene (Compound 54) (32 mg, 30 μmol) in 50% yield. $^1$H nmr (16 acetone): δ=7.82 (s, 4H); 7.36 (s, 4H); 6.32 (s, 2H); 4.62 (s, 4H); 4.57 (s, 4H); 4.01 (s, 4H); 3.75-3.6 (m, 16H); 3.11 (t, 4H); 2.41 (s, 12H) and 2.29 (m, 4H). $^{19}$F nmr (D6 acetone): δ=65.5 ppm. M.S. (ES)(M+Na)$^+$ 1095.3885 (Calc. $C_{52}H_{58}F_6N_6O_{12}Na$=1095.3900).

Example 27

Compounds 55, 56 and 57 were prepared using essentially the same method as described in example 26 for Compound 54 by using appropriate diols in carrying out step (ii) as described in example 25. The compounds were purified on silica gel and characterised by their nuclear magnetic resonance (nmr) spectra and mass spectral (MS) data. The nmr and MS data are recorded in Table 4 below.

Example 28

Preparation of 1,6-bis-[6-[4-(3-methylphenyl)-piperazin-1-yl]-pyridazin-3-yloxy]-3-oxapentyl-5-aminocarbonylamino]hexane (Compound 58)

(i) Preparation of 3-[5-amino-3-oxapentyloxy]-6-[4-(3-methylphenyl)-piperazin-1-yl]-pyridazine 3-Chloro-6-[4-(3-methylphenyl)-1-piperazinyl]pyridazine (300 mg, 1 mmol) was added to a solution of sodium metal (140 mg, 6 mmol) in 2-(2-aminoethoxy)ethanol (3 ml) and the solution was heated at 100° C. under an atmosphere of argon for 6 hr. Most of the excess aminoethoxyethanol was removed by distillation under reduced pressure and ice-water was added to the residue to give a thick white precipitate. The cold suspension was stirred for a few minutes and then filtered to give the product amine as a sticky white solid (240 mg). $^1$H NMR ($CDCl_3$): δ 2.3 (s, 3H); 2.9 (t, 2H); 3.3 (m, 4H); 3.5-3.6 (m, 4H); 3.6-3.7 (4H); 3.75 (m, 2H); 3.8 (m, 2H); 4.6 (m, 2H); 6.7-6.8 (m, 3H); 6.9 (d, 1H); 7.1 (d, 1H); 7.1-7.2 (m, 1H).

(ii) Preparation of 6-bis-[6-[4-(3-methylphenyl]piperazin-1-yl]-pyridazin-3-yloxy]-3-oxapentyl-5-aminocarbonylamino]hexane (Compound 58)

1,6-Diisocyanatohexane (17 g, 0.1 mmol) was added with stirring to a solution of 3-[2-(2-aminoethoxy)ethoxy]-6-[4-(3-methylphenyl)-1-piperazinyl]pyridazine (70 mg, 0.2 mmol) in pyridine (10 ml) at room temperature. The reaction was heated to 50° C. for 2 hr, stirred at room temperature for 20 hr and then the pyridine was removed on a rotary evaporator. Toluene (2×10 ml) was added to the residue and then evaporated on the rotary evaporator. The residue was chromatographed on silica gel (9.5 g) using chloroform as eluent. The first compound to be eluted from the column was a white solid which was found to be the dimeric product 1,6-Bis-[6-[4-(3-methylphenyl)-1-piperazinyl]-3-pyridazinyl] oxyethoxyethylureido]hexane (Compound 58) (35 mg, 40%). $^1$H NMR ($CDCl_3$): δ 1.2-1.5 (m, 4H); 2.3 (s, 3H); 3.1 (t, 2H); 3.2-3.4 (m, 6H); 3.5-3.7 (m, 6H); 3.8 (m, 2H); 4.5 (m, 2H); 6.7-6.8 (m, 3H); 6.9 (d, 1H); 7.1 (m, 1H); 7.1-7.2 (m, 1H). Mass spectrum (ESI): 883.5 (M+1), 648.1, 469.2, 447.2, 442.27 (M/2+1).

Example 29

Dendrimer (Compound 59)

Thiophosgene (65 mg, 570 μmol) was added to a solution of Compound 17 (136 mg, 226 μmol) in DCM containing triethylamine (57 mg, 5701 mmol). The reaction was stirred at room temperature under argon for 1 hr, then the reaction was concentrated and chromatographed on silica gel (10 g), eluent 1% to 2.5% MeOH in DCM to give 3-(1-isothiocyanato-3,6,9,12,15,18-hexaoxanonadecyl)-5-[3-[2,6-dimethyl-4-phenylphenoxy]-propyl]-isoxazole (80 mg, 124 μmol) in 55% yield. $^1$H nmr ($CDCl_3$): δ=7.6-7.2 (m, 7H); 6.15 (s, 1H); 4.62 (s, 2H); 3.86 (t, 2H); 3.7-3.5 (m, 24H); 3.06 (t, 2H); 2.33 (s, 6H) and 2.22 (m, 2H). M.S. (ES)(M+

Na)$^+$ 665.2861 (Calc. $C_{34}H_{46}N_2O_8SNa$=665.2861). A solution of the isocyanate (80 mg, 124 μmol) in DMF (1.5 ml) was added to a solution of Starburst dendrimer generation 0 (10 mg, 19 μmol) in DMF (1 ml) containing triethylamine (12.5 mg, 124 μmol). The reaction was stirred at room temperature under argon overnight, then the reaction was concentrated and chromatographed on silica gel (10 g), eluent 10% MeOH in DCM to give dendrimer Compound 59 (24 mg, 8 μmol) in 42% yield. 1H mm ($CDCl_3$): δ=7.95 (NH); 7.60 (NH); 7.6-7.2 (m, 28H); 6.14 (s, 4H); 4.61 (s, 8H); 3.86 (t, 8H); 3.8-3.5 (m, 26H); 3.4 (br, 8H); 3.06 (t, 8H); 2.6 (br, 8H); 2.32 (s, 24H) and 2.22 (m, 8H). M.S. (ES)(M+2Na)$^{++}$ 1565.7771 (Calc. $C_{158}H_{232}N_{18}O_{36}S_4Na_2$=1565.7749)

Example 30

Preparation of 3-(1-(6-biotinamidohexyl)amido-3,6,9,12,15,18-hexaoxanonadecyl)-5-[3-[2,6-dimethyl-4-phenylphenoxy]propyl]-isoxazole (Compound 60)

Solid sulfosuccinimidyl 6-(biotinamido)hexanoate (150 mg, 0.27 mmol) was added slowly to a suspension containing compound 17 (75 mg, 0.134 mmol) and potassium carbonate (92 mg, 0.67 mmol) in DMF (1.5 ml). The reaction was allowed to stir overnight under argon, then partitioned between ethyl acetate (100 ml) and water (30 ml), washed with saturated bicarbonate and dried ($Na_2SO_4$). The crude product was adsorbed onto silica gel (2 g) and chromatography on silica gel (8 g) eluent 5%-10% MeOH/ gave 3-(1-(6-biotinamidohexyl)amido-3,6,9,12,15,18-hexaoxanonadecyl)-5-[3-[2,6-dimethyl-4-phenylphenyoxy]-propyl]-isoxazole 60 (50 mg, 0.05 mmol) in 40% yield. $^1$Hnmr 6=1.8-1.3 (br, 12H); 2.24 (m, 2H); 2.32 (s, 6H); 3.06 (m, 2H); 3.3-2.9 (br, 9H); 3.45 (br, 2H); 3.65 (s, 22H); 3.87 (m, 2H); 4.5 (br, 2H); 4.61 (s, 2H); 6.14 (s, 1H); 7.27 (m, 3H); 7.40 (m, 2H) and 7.53 (m, 2H). MS (ESI) 940 (M+H)$^+$.

Example 31

Preparation of 1,2-bis[4-[2-[1-(6-methyl-3-pyridazinyl)-4-piperidinyl]-ethoxy]benzalde]-O-ethyl oxime (Compound 61)

(i) Preparation of 4-[2-[1-(6-methyl-3-pyridazinyl)-4-piperidinyl]ethoxy]benzalde A solution of diisopropylazadicarboxylate (0.69 g, 3.4 mmol) in THF (3 ml) was added to a solution containing 1-(6-methyl-3-pyridazinyl)-4-piperidine ethanol (500 mg, 2.3 mmol) prepared as in U.S. Pat. No. 4,992,433, triphenylphosphine and 4-hydroxybenzaldehyde (345 mg, 2.8 mmol) in anhydrous THF (20 ml). The orange reaction was allowed to stir overnight under argon, then adsorbed onto silica gel (3 g) and chromatography on silica gel (80 g) eluent 3:1 chloroform/ethyl acetate gave 4-[2-[1-(6-methyl-3-pyridazinyl)-4-piperidinyl]-ethoxy]benzalde (470 mg, 1.45 mmol) in 56% yield. $^1$Hnmr 6=1.3 (m, 2H); 1.9 (m, 3H); 2.71 (s, 3H); 3.03 (m, 2H); 4.13 (m, 2H); 4.39 (m, 2H) 7.00 (m, 2H); 7.17 (d, 1H); 7.31 (d, 1H); 7.83 (m, 2H) and 9.89 (s, 1H).

(ii) Preparation of 1,2-bis-[4-[2-[1-(6-methyl-3-pyridazinyl)-4-piperidinyl]-ethoxy]benzalde]-O-ethyl oxime 61

A suspension containing 1,2-diaminooxyethane bis hydrochloride (8 mg, 0.05 mmol), prepared according to the literature *J. Org. Chem.* (1984) 49 4487 *Tetrahedron Lett.* (1984) 25 2093, 4-[2-[1-(6-methyl-3-pyridazinyl)-4-piperidinyl]-ethoxy]benzalde (32 mg, 0.1 mmol) and sodium carbonate (26 mg, 0.25 mmol) in DMF (1 ml) was stirred at room temperature overnight. The reaction was filtered and adsorbed onto silica (1 g) then chromatography on silica gel (4 g) ethyl acetate/hexane gave 1,2-bis[4-[2-[1-(6-methyl-3-pyridazinyl)-4-piperidinyl]-ethoxy]benzalde]-O-ethyl oxime 61.

TABLE 4

| Compound Number | MS data (ESI) | NMR data: proton ($^1$H) and fluorine ($^{19}$F) chemical shifts δ in ppm ($CDCl_3$) |
|---|---|---|
| 8 | (M + Na)$^+$ = 492.2384 | $^1$H: 7.6-7.2(m, 7H); 6.17(s, 1H); 4.63(s, 2H); 3.86 (t, 2H); 3.8-3.6(m, 12H); 3.06(t, 2H); 2.33(s, 6H) and 2.23(m, 2H) |
| 9 | (M + Na)$^+$ = 536.2609 | $^1$H: 7.6-7.2(m, 7H); 6.16(s, 1H); 4.62(s, 2H), 3.86 (t, 2H); 3.66(m, 16H); 3.06(t, 2H); 2.32(s, 6H) and 2.22(m, 2H). |
| 10 | (M + Na)$^+$ = 624.3134 | $^1$H: 7.6-7.2(m, 7H); 6.14(s, 1H); 4.61(s, 2H), 3.86 (t, 2H); 3.65(m, 24H); 3.06(t, 2H); 2.33(s, 6H) and 2.22(m, 2H). |
| 11 | (M + Na)$^+$ = 756.3890 | $^1$H: 7.6-7.2(m, 7H); 6.14(s, 1H); 4.61(s, 2H), 3.87 (t, 2H); 3.75-3.6(m, 31H); 3.06(t, 2H); 2.32(s, 6H) and 2.22(m, 2H). |
| 12 | (M + Na)$^+$ = 932.4922 | $^1$H: 7.6-7.2(m, 7H); 6.14(s, 1H); 4.61(s, 2H), 3.86 (t, 2H); 3.75-3.6(m, 34H); 3.06(t, 2H); 2.32(s, 6H) and 2.22(m, 2H). |
| 13 | (M + Na)$^+$ = 1328.7350 | $^1$H: 7.6-7.2(m, 7H); 6.14(s, 1H); 4.61(s, 2H), 3.86 (t, 2H); 3.75-3.6(m, 87H); 3.05(t, 2H); 2.32(s, 6H) and 2.22(m, 2H). |
| 15 | (M + H)$^+$ = 469.2718 | ($CD_3OD$)$^1$H: 7.6-7.2(m, 7H); 6.28(s, 1H); 4.58(s, 2H), 3.84(t, 2H); 3.6(m, 8H); 3.49(t, 2H); 3.06(t, 2H); 2.75(br, 2H); 2.29(s, 6H) and 2.19(m, 2H). |
| 16 | (M + H)$^+$ = 513.2949 | ($CD_3OD$)$^1$H: 7.6-7.2(m, 7H); 6.28(s, 1H); 4.58(s, 2H), 3.85(t, 2H); 3.7-3.55(m, 12H); 3.49(t, 2H); |

TABLE 4-continued

| Compound Number | MS data (ESI) | NMR data: proton ($^1H$) and fluorine ($^{19}F$) chemical shifts δ in ppm ($CDCl_3$) |
|---|---|---|
| | | 3.07(t, 2H); 2.75(br, 2H); 2.30(s, 6H) and 2.20(m, 2H). |
| 17 | $(M + H)^+$ = 601.3471 | ($CD_3OD$)$^1H$: 7.6-7.2(m, 7H); 6.28(s, 1H); 4.59(s, 2H), 3.84(t, 2H); 3.7-3.5(m, 22H); 3.06(t, 2H); 2.93(br, 2H); 2.29(s, 6H) and 2.20(m, 2H). |
| 20 | $(M + H)^+$ = 511.2834 | $^1H$: 7.6-7.2(m, 7H); 6.4(NH); 6.13(s, 1H); 4.64(s, 2H), 3.86(t, 2H); 3.7-3.6(m, 8H); 3.56(m, 2H); 3.45(m, 2H); 3.06(t, 2H); 2.33(s, 6H); 2.22(m, 2H) and 1.98(s, 3H). |
| 21 | $(M + Na)^+$ = 577.2886 | $^1H$: 7.6-7.2(m, 7H); 6.4(NH); 6.14(s, 1H); 4.61(s, 2H), 3.86(t, 2H); 3.7-3.5(m, 14H); 3.44(m, 2H); 3.06(t, 2H); 2.33(s, 6H); 2.22(m, 2H) and 1.97(s, 3H). |
| 22 | $(M + Na)^+$ = 665.3384 | $^1H$: 7.6-7.2(m, 7H); 6.4(NH); 6.14(s, 1H); 4.61(s, 2H), 3.86(t, 2H); 3.7-3.5(m, 22H); 3.44(m, 2H); 3.06(t, 2H); 2.33(s, 6H); 2.22(m, 2H) and 1.98(s, 3H). |
| 24 | $(M + Na)^+$ = 552.1924 | $^1H$: 7.78(s, 2H); 6.17(s, 1H); 4.63(s, 2H); 3.88(t, 2H); 3.8-3.6(m, 12H); 3.06(t, 2H); 2.33(s, 6H) and 2.23(m, 2H). $^{19}F$: −65.9(95%) |
| 25 | $(M + Na)^+$ = 596.2194 | $^1H$: 7.77(s, 2H); 6.16(s, 1H); 4.61(s, 2H); 3.87(t, 2H); 3.75-3.55(m, 16H); 3.05(t, 2H); 2.33(s, 6H) and 2.23(m, 2H). $^{19}F$: −65.9(92%) |
| 26 | $(M + Na)^+$ = 684.2710 | $^1H$: 7.77(s, 2H); 6.15(s, 1H); 4.61(s, 2H); 3.88(t, 2H); 3.75-3.55(m, 24H); 3.05(t, 2H); 2.33(s, 6H) and 2.23(m, 2H). $^{19}F$: −65.9(96%) |
| 33 | $(M + Na)^+$ = 855.4160 | $^1H$: 7.6-7.2(m, 14H); 6.14(s, 2H); 4.61(s, 4H); 3.86(t, 4H); 3.65(s, 16H); 3.06(t, 4H); 2.32(s, 12H) and 2.22 (m, 4H). |
| 34 | $(M + Na)^+$ = 943.4737 | $^1H$: 7.6-7.2(m, 14H); 6.14(s, 2H); 4.61(s, 4H); 3.86(t, 4H); 3.65(m, 24H); 3.06(t, 4H); 2.32(s, 12H) and 2.22(m, 4H). |
| 35 | $(M + Na)^+$ = 1075.5515 | $^1H$: 7.6-7.2(m, 14H); 6.14(s, 2H); 4.61(s, 4H); 3.86(t, 4H); 3.7-3.6(m, 29H); 3.06(t, 4H); 2.32(s, 12H) and 2.22(m, 4H). |
| 36 | $(M + Na)^+$ = 1251.6609 | $^1H$: 7.6-7.2(m, 14H); 6.14(s, 2H); 4.61(s, 4H); 3.86(t, 4H); 3.7-3.6(m, 50H); 3.06(t, 4H); 2.32(s, 12H) and 2.22(m, 4H). |
| 37 | $(M + Na)^+$ = 1647.9894 | $^1H$: 7.6-7.2(m, 14H); 6.14(s, 2H); 4.61(s, 4H); 3.87(t, 4H); 3.7-3.6(m, 85H); 3.06(t, 4H); 2.32(s, 12H) and 2.22(m, 4H). |
| 39 | $(M + Na)^+$ = 1063.5182 | $^1H$: 7.6-7.2(m, 18H); 6.14(s, 2H); 4.61(s, 4H); 4.54 (s, 4H); 3.85(t, 4H); 3.7-3.55(m, 24H); 3.05(t, 4H); 2.32(s, 12H) and 2.22(m, 4H). |
| 40 | $(M + Na)^+$ = 1151.5792 | $^1H$: 7.6-7.2(m, 18H); 6.14(s, 2H); 4.61(s, 4H); 4.54 (s, 4H); 3.86(t, 4H); 3.7-3.55(m, 32H); 3.06(t, 4H); 2.32(s, 12H) and 2.22(m, 4H). |
| 41 | $(M + Na)^+$ = 1327.7009 | $^1H$: 7.6-7.2(m, 18H); 6.14(s, 2H); 4.61(s, 4H); 4.54 (s, 4H); 3.86(t, 4H); 3.7-3.55(m, 48H); 3.06(t, 4H); 2.32(s, 12H) and 2.22(m, 4H). |
| 43 | $(M + Na)^+$ = 1133.5605 | $^1H$: 7.6-7.2(m, 17H); 6.14(s, 1H); 6.08(s, 1H); 4.64 (s, 2H); 4.60(s, 2H); 3.84(m, 4H); 3.7-3.5(m, 20H); 3.40(m, 4H); 3.03(m, 4H); 2.31(s, 12H); 2.18(m, 4H) and 2.11(s, 3H) |
| 44 | $(M + Na)^+$ = 1221.6117 | $^1H$: 7.6-7.2(m, 17H); 6.08(s, 2H); 4.56(s, 2H); 4.55 (s, 2H); 3.84(t, 4H); 3.7-3.5(m, 28H); 3.40(m, 4H); 3.02(m, 4H); 2.32(s, 12H); 2.18(m, 4H) and 2.14(s, 3H) |
| 45 | $(M + Na)^+$ = 1397.7187 | $^1H$: 7.6-7.0(m, 17H); 6.12(s, 2H); 4.57(s, 4H); 3.85 (s, 2H); 3.7-3.5(m, 44H); 3.41(m, 4H); 3.05(m, 4H); 2.32(s, 12H); 2.21(m, 4H) and 2.16(s, 3H) |
| 46 | $(M + Na)^+$ = 1121.5386 | $^1H$: 7.6-7.0(m, 22H); 6.10(s, 2H); 4.63(s, 4H); 3.84 (s, 4H); 3.82(s, 2H) 3.7-3.5(m, 12H); 3.44(m, 4H); 3.06(m, 4H); 2.31(s, 12H) and 2.21(m, 4H) |
| 47 | $(M + Na)^+$ = 1209.5927 | $^1H$: 7.6-7.0(m, 22H); 6.11(s, 2H); 4.66(s, 4H); 3.83 (s, 4H); 3.81(s, 2H); 3.7-3.5(m, 20H); 3.41(t, 4H); 3.03(t, 4H); 2.31(s, 12H) and 2.17(m, 4H) |
| 48 | $(M + Na)^+$ = 1297.6447 | $^1H$: 7.6-7.0(m, 22H); 6.03(s, 2H); 4.54(s, 4H); 3.82 (m, 6H); 3.8-3.5(m, 28H); 3.40(m, 4H); 2.99(t, 4H); 2.31(s, 12H) and 2.16(m, 4H) |
| 49 | $(M + Na)^+$ = 1473.7506 | $^1H$: 7.6-7.0(m, 22H); 6.11(s, 2H); 4.56(s, 4H); 3.82 (m, 6H); 3.75-3.5(m, 44H); 3.40(t, 4H); 3.05(t, 4H); 2.32(s, 12H) and 2.21(m, 4H) |

TABLE 4-continued

| Compound Number | MS data (ESI) | NMR data: proton ($^1H$) and fluorine ($^{19}F$) chemical shifts δ in ppm ($CDCl_3$) |
|---|---|---|
| 51 | $(M + Na)^+$ = 931.3059 | (D6 acetone)$^1H$: 7.82(s, 4H); 6.34(s, 2H); 4.61(s, 4H); 4.02(t, 4H); 3.69(s, 8H); 3.64(s, 4H); 3.13(t, 4H); 2.41(s, 12H); 2.30(m, 4H). $^{19}F$: −65.46. |
| 52 | $(M + Na)^+$ = 975.3288 | (D6 acetone)$^1H$: 7.78(s, 4H); 6.30(s, 2H); 4.56(s, 4H); 3.97(t, 4H); 3.7-3.5(m, 16H); 3.09(t, 4H); 2.37 (s, 12H); 2.26(m, 4H). $^{19}F$: −65.28. |
| 53 | $(M + Na)^+$ = 1063.3819 | (D6 acetone)$^1H$: 7.78(s, 4H); 6.31(s, 2H); 4.57(s, 4H); 3.98(t, 4H); 3.7-3.5(m, 24H); 3.09(t, 4H); 2.37 (s, 12H) and 2.26(m, 4H). $^{19}F$: −65.31. |
| 55 | $(M + Na)^+$ = 1183.4427 | (D6 acetone)$^1H$: 7.78(s, 4H); 7.31(s, 4H); 6.30(s, 2H); 4.56(s, 4H); 4.52(s, 4H); 3.96(t, 4H); 3.75-3.6 (m, 24H); 3.08(t, 4H); 2.37(s, 12H) and 2.25(m, 4H). $^{19}F$: −65.5 |
| 56 | $(M + Na)^+$ = 1271.5009 | (D6 acetone)$^1H$: 7.83(s, 4H); 7.46(s, 4H); 6.34(s, 2H); 4.60(s, 4H); 4.56(s, 4H); 4.01(t, 4H); 3.75-3.6 (m, 32H); 3.13(t, 4H); 2.41(s, 12H) and 2.09(m, 4H). $^{19}F$: −65.27 |
| 57 | $(M + Na)^+$ = 1447.5934 | (D6 acetone)$^1H$: 7.84(s, 4H); 7.37(s, 4H); 6.34(s, 2H); 4.61(s, 4H); 4.58(s, 4H); 4.03(t, 4H); 3.7-3.6(m, 48H); 3.13(t, 4H); 2.42(s, 12H) and 2.3(m, 4H). $^{19}F$: −65.44 |

Example 32

Anti-HRV Activity in Mammalian Cell Culture Assays Inhibition of Viral Cytopathic Effect (CPE) and Measurement of Cytotoxicity The ability of compounds to suppress virus replication and thereby protect cells from HRV-induced CPE was measured using human embryo lung (MRC-5) and human epidermoid carcinoma of the mouth (KB) cells infected with HRV type 1A and HRV type 2, respectively. Cells grown in 96 well tissue culture plates using conventional mammalian tissue culture medium (such as minimum essential medium) supplemented with fetal calf serum were used in an assay essentially similar to that described by Sidwell and Huffman (Applied Microbiology, 22, 797-801 (1971)). Test compounds were dissolved in 100% anhydrous dimethyl sulfoxide and serially diluted in tissue culture medium. The antiviral potency of the test compounds was assessed by exposing replicate tissue culture wells to a selected dilution series of between 6 and 7 compound concentrations in the presence of sufficient test virus to invoke significant CPE over the course of the assay. Control cells were also exposed to identical concentrations of compounds in the absence of virus or were infected with virus under the same conditions but in the absence of compounds. Compounds of established anti-HRV efficacy (enviroxime, ribavirin and pirodavir) were assayed by identical procedures in parallel to the test compounds. Tissue culture media were identically supplemented to maintain cell viability and support viral growth while suppressing bacterial growth over the period of the assay (supplements: 2% fetal calf serum, 0.01% sodium bicarbonate, 50 g/ml gentamicin, 5 M magnesium chloride, 10 mM of zinc chloride). The assays were incubated at 37° C. in a 5% $CO_2$ atmosphere until significant CPE was observed by microscopic examination of the untreated, HRV infected control cells (generally between 5 and 8 days). At this time all infected cultures were examined by eye using a light microscope and CPE scored on a scale of 0 (no CPE) to 4 (maximum CPE). Uninfected treated cultures were similarly scored for cytotoxic effects (eg. cell enlargement, granularity, rounding, detachment). These scores were used to generate $EC_{50}$ (concentration of compound yielding 50% antiviral efficacy) and $CC_{50}$ (concentration of compound yielding 50% cytotoxicity) values by line regression analysis from plots of compound concentration versus % CPE or % cytotoxicity, respectively. As an alternative to a $CC_{50}$ value, cytoxicity in some cases was expressed as the Minimum Toxic Concentration (MTC). The MTC corresponds to the lowest compound concentration at which cytotoxic effects were observed.

Vital dye staining to measure cell viability was also used to quantify CPE and cytotoxic effects. The vital dye technique was based on either neutral red uptake (Modification of the method of McManus, Appl. Environment. Microbiol., 31, 35-38, 1976) or XXT metabolism. After the assay had been scored by eye with the aid of a microscope, 100 1 of neutral red (NR) solution (0.34% NR in phosphate buffered saline (PBS)) was added to each well and mixed gently. The assays were returned to the 37° C. incubator for 2 hours to facilitate uptake of the NR by viable cells. The medium/NR mixture was then aspirated from the surface of the cells, which were washed twice with PBS. 0.25 ml of absolute ethanol containing Sorensen's citrate buffer I, was added with gentle mixing and the assays incubated at room temperature in the dark for 30 minutes to dissolve the NR. NR staining of viable cells was then quantified spectrophotometrically by measuring the colour density of the NR solution using a BioTek EL-309 microplate reader at dual wavelengths of 540 and 405 nm. The differences in the two readings were automatically determined to eliminate background errors. $EC_{50}$ and $CC_{50}$ values were determined by regression analysis matching compound concentration to NR staining. The XTT method involved use of a solution of XTT (1 mg/ml in culture media) which was added to each well and the plates incubated at 37° C. for 4 hours. XTT metabolism was measured spectrophotometrically using a similar method to that described above except that the dual wavelengths were 450 nm and 650 nm. $EC_{50}$ and $CC_{50}$ values were determined by regression analysis using a similar method to that described above.

The results are shown in Table 5 below. Selectivity indices (SI) are the $CC_{50}$ or MTC divided by the $EC_{50}$.

TABLE 5

| Compound number | Activity on Rhinovirus Type 2 EC$_{50}$ (μg/ml) | CC$_{50}$ | SI | Activity on Rhinovirus Type 1A EC$_{50}$(μg/ml) | CC$_{50}$ | SI |
|---|---|---|---|---|---|---|
| 6 | <0.005 | >5 | >1000 | 0.16 | >50 | >320 |
| 8 | 0.001 | 5 | 5000 | 0.59 | 22.7 | 38.61 |
| 10 | 0.1 | 5 | 50 | >50 | 19 | — |
| 32 | 0.1 | >5 | >50 | 0.32 | >50 | >156.32 |
| 34 | 0.09 | >0.5 | >5 | >50 | 10.9 | — |
| 48 | 0.6 | >5 | >8 | 3.85 | 30.6 | 7.75 |
| 19 | <0.005 | 2 | >400 | 0.87 | 5.79 | 6.66 |
| 50 | 0.02 | 2 | 100 | 0.06 | 10 | 167 |
| 56 | 0.09 | 2 | 22 | 1.8 | 10 | 6 |
| 24 | 0.04 | >1 | >30 | 0.21 | 5.28 | 25.71 |
| 59 | 10 | >50 | >5 | | | |
| Controls: | | | | | | |
| Pleconaril | 0.05 | 0.5 | 10 | 0.02 | 10 | 500 |
| Pirodavir | 0.003 | >1 | >300 | 0.02 | >10 | 555.74 |
| Ribavirin | | | | 1.93 | 98.3 | 51.03 |
| Enviroxime | | | | 0.006 | 0.49 | 75.91 |

Example 33

Activity against Enteroviruses in Mammalian Cell Culture Assays Compounds 50 and 56 of the Invention were Tested Against Other Picornaviruses Using Similar cell based assays to those described in example 30 above and the results are shown in Table 6 below:

at least two capsid binding moieties, and a non-polymeric backbone or core, wherein the at least two capsid binding moieties are covalently attached to the non-polymeric backbone or core, and wherein the at least two capsid binding moieties are the same or different and individually selected from formula (I):

$$Ar^1(X)_mW(Y)_nAr^2 \quad (I)$$

where $Ar^1$ and $Ar^2$ are optionally substituted, aromatic mono-, bi- or tri-cyclic rings or ring systems, which may be the same or different, said aromatic rings or ring systems having 3 to 15 carbon atoms, and in the case of heteroaromatic rings, containing one or more heteroatoms selected from N, S or O;

X and Y are independently selected from O, S, CO, C(O)O, CONR or NR, where R is hydrogen or $C_{1-6}$ alkyl;

W is selected from the group consisting of optionally substituted straight chain or branched alkylene groups of from 1 to 10 carbon atoms which may have one or more double or triple bonds; optionally substituted alkyleneoxy groups; optionally substituted aryl groups; and optionally substituted aliphatic rings which may be saturated or unsaturated and which may include one or more heteroatoms selected from O, S and N; and m and n are independently 0 or 1;

said compound being linked to a detectable label.

TABLE 6

| Compound Number | Activity on Enterovirus 70 EC$_{50}$(μg/ml) | CC$_{50}$ | SI | Activity on Coxsackie A21 EC$_{50}$(μg/ml) | CC$_{50}$ | SI | Activity on Echo 21 EC$_{50}$(μg/ml) | CC$_{50}$ | SI |
|---|---|---|---|---|---|---|---|---|---|
| 50 | >50 | >50 | — | 0.35 | >50 | >143.03 | 0.0006 | 46.3 | >10000 |
| 56 | 2.88 | >50 | >17.3 | 0.36 | 11.1 | 30.51 | 0.0026 | 7.93 | 3000 |
| Controls: | | | | | | | | | |
| Pleconaril | 0.28 | >50 | >178.89 | 0.0033 | >50 | >15057 | >0.00016 | 31.3 | >10000 |
| Ribavirin | >100 | >100 | — | >100 | >100 | — | 3 | 56.6 | 19 |
| Enviroxime | 0.21 | 4.11 | 19.35 | 0.39 | 9.55 | 24.25 | 0.03 | 0.45 | 15 |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. An agent for detecting rhinoviral infection in humans comprising a compound capable of binding to a rhinovirus (HRV) capsid, the compound comprising:

2. The agent of claim 1 wherein the at least two capsid binding moieties are capable of simultaneously binding within separate hydrophobic pockets on the same or different HRV capsids.

3. The agent of claim 1 wherein the compound has a molecular weight of less than 10,000.

4. The agent of claim 2 wherein the non-polymeric backbone or core is selected from the group consisting of:

a straight chain, branched or cyclic $C_1$-$C_{70}$ alkyl optionally including one or more double or triple bonds and optionally including one or more heteroatoms selected from oxygen, sulfur and nitrogen;

oligomers of amino acids, acrylamide, N-substituted acrylamides, acrylic acid, alkeneoxy moieties, aminoalkanoic acids, and carbohydrates;

small to medium sized dendritic cores; and cyclodextrins.

5. The agent of claim 1 wherein the non-polymeric backbone or core comprises two or more linker groups to which the two or more capsid binding moieties are attached, each linker group being capable of passing through the picornaviral pore and having a length sufficient to allow the attached capsid binding moiety to reach inside and bind within a hydrophobic pocket of the rhinoviral capsid.

6. The agent of claim 5 wherein the two or more linker groups are the same or different and independently selected from the group consisting of alkyl, aryl, alkenyl, alkynyl, alkyleneoxy, amino acids, alkylamino, alkylcarbonyl, alkylcarboxy, alkoxy, alkylurea, alkylhydrazide and combinations thereof.

7. The agent of claim 5 wherein the non-polymeric backbone or core and/or the two or more of the linker groups comprises a functional group which imposes restrictions on available degrees of freedom.

8. The agent of claim 7 wherein the functional group is an alkenyl, aryl or amido group.

9. The agent of claim 2 wherein the two or more capsid binding moieties comprise between two and ten capsid binding moieties.

10. The agent of claim 9 comprising five capsid binding moieties located on the non-polymeric backbone or core such that they bind within the five hydrophobic pockets located about one of the fivefold icosahedral axes of the rhinoviral capsid.

11. The agent of claim 1 wherein the two or more capsid binding moieties are covalently attached to the non-polymeric backbone or core such that the compound is in the form of a dimer with a center of symmetry.

12. The agent of claim 1 wherein W is selected from the group consisting of $-(CH_2)_m-$ where m is 1 to 9; and $-(CH_2)_p-Z-(CH_2)_q-$ where p and q are independently 0 to 4, and Z is an optionally substituted $C_2$-$C_6$ alkylene group containing one or more double or triple bonds or a five or six membered aromatic or aliphatic ring which may contain one to four heteroatoms selected from O, S and N.

13. The agent of claim 1 wherein the divalent spacer group is selected from the group consisting of $-(CH_2)_m-$ where m is 2 to 7; and a group of the formula $-(CH_2)_p-Z-(CH_2)_q-$ where p and q are independently 0 to 3, and Z is a five or six membered aromatic or aliphatic ring containing from 1 to 2 N atoms or a group of the formula $-(CH{=}CH)_n-$ where n is 1 to 3.

14. The agent of claim 2 wherein each of the two or more capsid binding moieties is covalently attached to the non-polymeric backbone or core at a position on the two or more capsid binding moieties located in the region at the end of the two or more capsid binding moieties which lies near the pore of the hydrophobic pocket (heel region) during binding.

15. The agent of claim 14 wherein each of the two or more capsid binding moieties contains a functional group at its heel region capable of forming a covalent bond with the non-polymeric backbone or core, wherein the functional group is located in the region at the end of the capsid binding moiety which lies near the pore of the hydrophobic pocket (heel region) during binding.

16. The agent of claim 15 wherein the functional group is selected from the group consisting of a hydroxy, amine, azide, aldehyde, carboxylic acid, amide, ester, hydrazide, oxime ether, imidazolide, hydroxamate, thioester, mercapto, halide, ketone, hydrazine, iscyanate and isothiocyanate.

17. The agent of claim 15 wherein the covalent bonds between the at least two capsid binding moieties and the non-polymeric backbone or core are formed between the functional group and a complementary functional group on a linker group of the non-polymeric backbone or core.

18. A method for the diagnosis of human rhinoviral infections, comprising:

preparing a biological sample suspected of containing human rhinoviral virus, incubating the sample with an agent of any one of claims 1, 2-11, 12, 13 and 14-17, the incubation occurring for a time and under conditions sufficient to form a human rhinovirus-agent complex, and detecting the presence or absence of such human rhinovirus-agent complex.

* * * * *

UNITED STATES PATENT AND TRADEMARK OFFICE
CERTIFICATE OF CORRECTION

PATENT NO. : 7,371,755 B1
APPLICATION NO. : 10/088282
DATED : May 13, 2008
INVENTOR(S) : Guy Krippner et al.

It is certified that error appears in the above-identified patent and that said Letters Patent is hereby corrected as shown below:

Column 17 and 18
Line 58,

"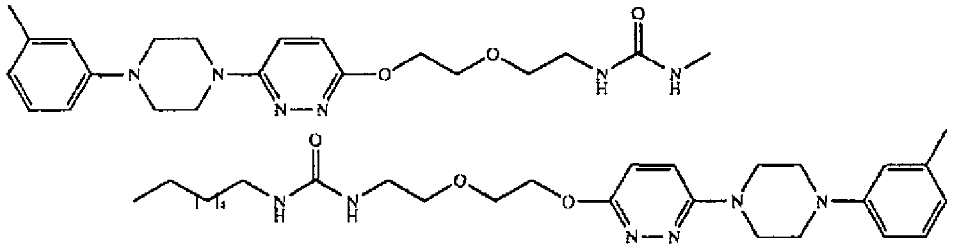"

should read as

-- 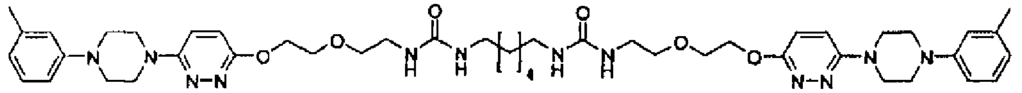 --

Column 23
Line 60, "12-tetraoxamidecyl)-" should read as -- 12-tetraoxatridecyl)- --

Column 23
Line 61, "2,6-dichloro-4-(4,5-dihydro-2-oxazolyl)" should read as
-- 2,6-dichloro-4(4,5-dihydro-2-oxazolyl) --

Column 23
Lines 64-65, "2,6-dichloro-4-(4,5-dihydro-2-oxazolyl)" should read as
-- 2,6-dichloro-4(4,5-dihydro-2-oxazolyl) --

Column 23
Line 65, "(540 mg, 1,25 μmnol)" should read as -- (540 mg, 1.25 mmol) --

Column 24
Line 9, "$^1$H mm (D6 acetone)" should read as -- $^1$H nmr (D6 acetone) --

Column 24
Line 25, "12-tetraoxamidecyl)-" should read as -- 12-tetraoxatridecyl)- --

UNITED STATES PATENT AND TRADEMARK OFFICE

CERTIFICATE OF CORRECTION

PATENT NO. : 7,371,755 B1 
APPLICATION NO. : 10/088282
DATED : May 13, 2008
INVENTOR(S) : Guy Krippner et al.

It is certified that error appears in the above-identified patent and that said Letters Patent is hereby corrected as shown below:

Column 24
Lines 35-36, "12-tetraoxamidecyl)-" should read as -- 12-tetraoxatridecyl)- --

Column 24
Lines 38-39, "12-tetraoxamidecyl)-" should read as -- 12-tetraoxatridecyl)- --

Column 24
Lines 49-50, "12-tetraoxamidecyl)-" should read as -- 12-tetraoxatridecyl)- --

Column 24
Lines 64-65, "12-tetraoxamidecyl)-" should read as -- 12-tetraoxatridecyl)- --

Column 25
Lines 9-10, "12-tetraoxamidecyl)-" should read as -- 12-tetraoxatridecyl)- --

Column 25
Line 18, "a solution of Compound 2 (25 mmol) in acetone (1 ml)" should read as -- a solution of Compound 2 (25 μmol) in acetone (1 ml) --

Column 25
Line 23, "12-tetraoxamidecyl)-" should read as -- 12-tetraoxatridecyl)- --

Column 25
Line 29, "(m, 2H)" should read as -- (m, 12H) --

Column 25
Lines 35-36, "12-tetraoxamidecyl)-" should read as -- 12-tetraoxatridecyl)- --

Column 25
Line 45, "(m, 2H)" should read as -- (m, 12H) --

Column 25
Line 47, "(m, 8H)" should read as -- (m, 18H) --

Column 26
Line 4, "dichloromethanelhexanes to give" should read as -- dichloromethane/hexanes to give --

UNITED STATES PATENT AND TRADEMARK OFFICE

CERTIFICATE OF CORRECTION

PATENT NO. : 7,371,755 B1
APPLICATION NO. : 10/088282
DATED : May 13, 2008
INVENTOR(S) : Guy Krippner et al.

It is certified that error appears in the above-identified patent and that said Letters Patent is hereby corrected as shown below:

Column 26
Line 27, "6.13 (s, 1);" should read as -- 6.13 (s, 1H); --

Column 29
Line 33, "(55 mg, 0.1 IImmol)" should read as -- (55 mg, 0.11 mmol) --

Column 29
Line 49, "The mm and MS" should read as -- The nmr and MS --

Column 32
Line 39, "(19 mg, 20 mmol)" should read as -- (19 mg, 20 μmol) --

Column 33
Line 50, "(38 mg, 189 mmol)" should read as -- (38 mg, 189 μmol) --

Column 35
Line 9, "magnetic resonance (mm) spectra and mass spectral data" should read as -- magnetic resonance (nmr) spectra and mass spectral data --

Column 36
Line 33, "(17 g, 0.1 mmol)" should read as -- (17 μl, 0.1 mmol) --

Column 36
Line 59, "(57 mg, 5701 mmol)" should read as -- (57 mg, 570 μmol) --

Column 37
Line 35, "$^1$Hnmr 6=1.8-1.3" should read as -- $^1$Hnmr δ=1.8-1.3 --

UNITED STATES PATENT AND TRADEMARK OFFICE

CERTIFICATE OF CORRECTION

PATENT NO. : 7,371,755 B1
APPLICATION NO. : 10/088282
DATED : May 13, 2008
INVENTOR(S) : Guy Krippner et al.

It is certified that error appears in the above-identified patent and that said Letters Patent is hereby corrected as shown below:

Column 38
Line 20, "$^1$Hnmr 6=1.3" is erroneous and instead should read as -- $^1$Hnmr $\delta$=1.3 --

Signed and Sealed this

Thirteenth Day of January, 2009

JON W. DUDAS
*Director of the United States Patent and Trademark Office*